United States Patent

Kohgami et al.

[11] Patent Number: 5,818,064
[45] Date of Patent: Oct. 6, 1998

[54] METHOD OF AND APPARATUS FOR PICKING UP AND DISPLAYING A STEREOSCOPIC IMAGE FROM AN OBJECT PERMEATED WITH RADIOACTIVE RAYS

[75] Inventors: Akihiko Kohgami, Fuchu; Tadaaki Hirai, Koganei; Keiji Umetani, Hino, all of Japan

[73] Assignee: Hitachi, Ltd., Tokyo, Japan

[21] Appl. No.: 659,832

[22] Filed: Jun. 7, 1996

Related U.S. Application Data

[63] Continuation of Ser. No. 301,772, Sep. 7, 1994, Pat. No. 5,583,345.

[30] Foreign Application Priority Data

Sep. 20, 1993 [JP] Japan ..................................... 5-232823

[51] Int. Cl.⁶ ..................................................... A61B 6/02
[52] U.S. Cl. .......................... 250/580; 250/336.1; 378/41
[58] Field of Search ................................. 250/336.1, 580; 378/41, 42

[56] References Cited

U.S. PATENT DOCUMENTS 5,583,345  12/1996  Kohgami et al. ....................... 250/580

FOREIGN PATENT DOCUMENTS 2564996  11/1985  France ....................................... 378/41
2546785  4/1977   Germany .................................. 378/41
1443551  7/1976   United Kingdom ..................... 378/41

Primary Examiner—Edward J. Glick
Attorney, Agent, or Firm—Antonelli, Terry, Stout, & Kraus, LLP

[57] ABSTRACT

A method and apparatus is provided for picking up and displaying a stereoscopic image from an object permeated with radioactive rays. A plurality of radioactive rays which are non-parallel with each other are directed substantially simultaneously onto an object to generate a plurality of superimposed images of the object. The superimposed images of the object are divided into a plurality of discrete partial images formed on a pickup surface, so that each point of the object will be included in a plurality of the partial images, with the partial images showing the same point being spatially separated from one another on the pickup surface. A stereoscopic image of the object is then reconstructed by processing the partial images so that partial images generated by each of the sources of the radioactive rays will be respectively used to generate separate images of the object to form the stereoscopic image of the object.

29 Claims, 15 Drawing Sheets

FLY'S EYE LENS BOARD
901
902

LINE SENSOR
1802
1801
102
A
101
B
100

METHOD OF AND APPARATUS FOR PICKING UP AND DISPLAYING A STEREOSCOPIC IMAGE FROM AN OBJECT PERMEATED WITH RADIOACTIVE RAYS

This is a continuation of application Ser. No. 08/301,772, filed Sep. 7, 1994 now U.S. Pat. No. 5,583,345.

BACKGROUND OF THE INVENTION

The present invention relates to a method of picking and displaying a stereoscopic image from an object permeated with radioactive rays. This method is useful, for example, for stereoscopically observing internal images of objects such as the human body and hand baggage, using X, γ and particle rays. The present invention is also directed to an apparatus for carrying out this method.

Unexamined Japanese Patent Publication No. 230194/1987, for example, discloses a method of picking up and displaying a stereoscopic image of an object permeated with radioactive rays and an apparatus for the same. The prior art to which the present invention pertains is intended to display a stereoscopic image through the steps of radiating an object with two X rays at different angles while shifting the shining time when the object is radiated with X rays from two X-ray sources. Images are generated from permeating the object at two separate times from two different angles on an image intensifier (I. I.) followed by converting the images into a stereoscopic one.

The drawback of the prior art mentioned above is that, since the two radioactive rays are subjected to time sharing, there develops a gap between two images resulting from permeating a moving object (e.g., the images from permeating the human heart).

SUMMARY OF THE INVENTION

An object of the present invention is to provide a method of picking up and displaying a stereoscopic image which is capable of reducing the gap between images resulting from moving objects, and an apparatus for the same.

In order to accomplish the above object, a pickup and display method comprises the steps of shining on an object a plurality of radioactive rays which are non-parallel with each other, spatially separating a plurality of images derived from the respective radioactive rays which permeate through the object so as to prevent the images from overlapping, dividing each image of the permeated object into a plurality of parts to make images (hereinafter called the partial images) on the pickup surface of a pickup device such as an image intensifier, and reconstructing each image from the partial images on the image pickup surface to display a stereoscopic image.

In order to accomplish the above object, a pickup and display apparatus for carrying out the process comprises a plurality of radiative ray sources for permeating an object, means for holding the object, means for spatially separating a plurality of images corresponding to the respective radioactive rays permeated through the object to prevent the images from overlapping and dividing each image into a plurality of partial images, the image pickup surface, means for reconstructing the respective images and means for stereoscopically displaying the image, the plurality of radiative ray sources being capable of radiating the plurality of radioactive rays which are non-parallel with each other, the means for separating and dividing the image being capable of installation between the object and the pickup surface of the image, the means for reconstructing and the respective images being capable of electrical connection with the image pickup surface.

In the pickup and display method according to the present invention, the object is radiated with radioactive rays such as X, γ and particle rays from the plurality of radioactive ray sources, and since the permeating radioactive rays are different in their angles, the radioactive rays are separated into subdivided areas so as to make striped or dotted images on one surface of the image pickup device. Consequently, the plurality of radioactive ray sources can be made to shine simultaneously, so that an accurate stereoscopic image of an area is obtainable, even though the area is moving. The reason that the subdivided images are striped is that, in a case where a plurality of radioactive ray sources are laterally arranged in a row, stereoscopic visual observation is accomplished by giving a parallax disparity in the horizontal direction only. In the case where the subdivided images are dotted, a plurality of radioactive ray sources are also arranged vertically to give the parallax disparity in the vertical direction as well. In order to make movement stereoscopic perception available even when an observer vertically moves his viewing point, it is only necessary to arrange the radioactive ray sources also in the vertical direction.

The emission of radioactive rays from the plurality of radioactive ray sources centers upon the same points of the object. In this case, the radioactive rays from the plurality of radioactive ray sources have Gaussian distribution of radioactive ray intensity toward the periphery from the center of the radioactive ray bundle. Therefore, the intensity will be maximized if the center of the radioactive ray bundle is set to the center of the object. In other words, radioactive rays showing flat distribution are emitted to the most important region of the object. A stable stereoscopic picture offering a greater signal to noise ratio is thus available.

The plurality of radioactive rays permeated through the object at different angles are converted into subdivided striped or dotted images corresponding to the plurality of radioactive ray sources by means of and at the back of a striped (the radioactive ray sources are laterally arranged in a row) or otherwise a meshed (the radioactive ray sources are disposed horizontally and vertically in a plurality of lines and rows) lead lattice. In this case, the plurality of radioactive ray sources are disposed within the view field formed by the lattice. Therefore, the stripe-to-stripe distance is widened when the lattice is onefold to provide a wide visual field. As the visual field is widened, the influence of noise also grows greater because of the scattered radioactive ray. Assuming that, for example, the distance from the radioactive ray source up to the image pickup surface of the image pickup device ranges from 1 to 2 m and that the distance between the two radioactive ray sources is equal to that of human binocular eyes, that is, 63 mm, a radioactive ray of the radioactive ray source makes an angle of 3.6 to 7.2 degrees with another ray. This means that the angle of the visual field remains within the range of the prior art, so that a stereoscopic image having the same signal to noise ratio as that in the prior art is obtainable.

The onefold lead lattice is used to separate the permeating radioactive rays having different angles in the subdivided space. However, the image pickup surface of the image pickup device is positioned behind the lattice and while the radioactive rays are passing to cover the distance from behind the lattice up to the image pickup surface of the pickup image, they will expand. In order for the radioactive rays having different angles to be completely separated after they have passed through the lattice, there has to be a margin in the expanse of the radioactive rays caused by the lead portion. In other words, the breadth g of the lead portion needs to be not smaller than a predetermined value, and the breadth g of the lead resulting from a simple geometric calculation should be at least not less than $g_0$.

In this case, there exists an area where the permeating radioactive rays having different angles are completely separated behind the lattice. On condition that the image pickup surface is placed in the area position $x_0$, the images of the object generated from the different radioactive ray sources can be completely separated from one another without allowing the plurality of permeating radioactive rays to overlap on the image pickup surface. The range of values $x_0$ in this case is set at $x_1<x_0<x_2$ using $x_1$, $x_2$ as noted previously. However, these relations may be obtained from simple geometric calculations.

When the radioactive rays are electron rays or particle rays such as ionized particles, any lattice similar to what has been mentioned above may be used to separate permeating particle rays having different angles in a subdivided space. In this case, a window in the lattice through which the rays pass needs to be a vacuum, gas or liquid to allow electron and ionized particle rays to pass therethrough. Moreover, the performance of such a lattice may deteriorate when the lattice is charged up since charged particles stick thereto. The whole lattice should be grounded in such a case to prevent such a charge up.

When the radioactive rays are charged particle rays, those particle rays having different angles may by separated effectively in the subdivided space through the steps of arranging striped or meshed electrodes, and applying different voltages to stripes of odd and even numbers to cause an electric field to be formed within the lattice. When the direction in which the incident angle of the particle ray substantially conforms to the direction in which force is received from the electric field, the particle ray is absorbed by the electrode and stopped, whereas when the direction in which the incident angle of the particle ray is substantially opposite to the direction in which the force is received from the electric field, the particle ray passes through the electrode lattice. The direction in which the force is received from the electric field in the lattice is alternately given in either direction in the striped or meshed window by applying different voltages to stripes of odd and even numbers. By virtue of this arrangement, if desired, the image pickup surface can be located directly in contact with the back of the electrode lattice since the charged particle rays are caused to either pass or stop passing through the lattice.

The motion locus of the charged particle within the electrode lattice can thus be obtained by solving Newton's motion equation in primary physics. The conditions under which the charge particle passes and stops passing through the electrode lattice are obtained from the motion equation. Assuming the difference between the voltages applied to the electrode stripes of odd and even numbers is 2 V, the permeation and stopping of the charged particle become uncontrollable regardless of the voltage supplied unless the dimensional ratio $\rho$ of the lattice is $(\frac{1}{4})$ cot $\theta<\rho<2$ cot $\theta$. Referring to other aspects of the invention, a description will be given of this fact later.

By ranging the value V over Vmin<V<Vmax using Vmin, Vmax at the value $\rho$ where the above condition is established, the permeation and stopping of the charged particle rays having different angles become controllable in the electrode lattice. When the image pickup surface is set to be in contact with the back of the electrode lattice, this range of values V is effective. When the charged particle rays having different angles are separated by utilizing the space at the back of the electrode lattice, the condition of the value V need not be satisfied.

In the case of radioactive rays generally including the fact that they are charged particle rays, only a few scattered radioactive rays are incident. In order to make the permeating radioactive rays from the plurality of radioactive ray sources efficiently incident on the lattice, the lattice should have directivity. For this purpose, a plurality of lattices having different pitches are overlapped, and the pitch of those which are closer to the object are made wider than that of those which are far therefrom.

If the relation between the pitch $t_2$ of a lattice close to the object and that $t_3$ of a lattice which is far therefrom is set at $mt_2=nt_3$ using the positive numbers m, n, the design and optical analysis of such lattices are facilitated. With m=1, n=2, for example, the lead portions that make up the front lattice are located to contact the lead portions that make up the rear lattice at all times, as shown in FIG. 12, for example. This greatly facilitates not only the optical design and analysis of the radioactive ray in the lead portions but also manufacture of the lattices.

As there are produced a plurality of restrictive directions of view fields in this case, the plurality of radioactive ray sources are prevented from interfering with each other by placing them in the regions where they are not overlapped, so that the images from the respective radioactive ray sources are substantially completely separated. Since the view field is narrow, the scattered radioactive ray is less affected and a stereoscopic image having a high signal to noise ratio is obtainable.

The permeating radioactive rays having different angles are passed through the lattice and then through the subdivided space in the rear of the lattice. However, the plurality of radioactive rays have their own angles and consequently there develops a region where the plurality of radioactive rays are overlapped as they move far from the lattice. The distance from the lattice in the region where the plurality of radioactive rays are overlapped is determined by the line breadth of the lattice. When the position of the image pickup surface of the image pickup device is set up closer to the lattice than the position where the radioactive rays are overlapped, the radioactive rays having different angles are prevented from interfering with each other and the objects permeated by rays from the plurality of radioactive ray sources can almost satisfactorily be separated.

However, the object has a finite size and consequently some distribution of angles of the radioactive rays develops from the radioactive ray sources. This becomes noise resulting from the interference of images from objects permeated by the plurality of radioactive ray sources. In this case, signals on the subdivided image pickup surface should be corrected. The method of correction comprises the steps of observing the signals from the respective radioactive ray sources without the object being present, followed by observing signals corresponding to the same radioactive ray sources on the subdivided image pickup surface when the object is present, multiplying the ratio of the former to the latter by the adjoining subdivided signals at the time the object is permeated, and subtracting the results from the respective subdivided signals. It is thus possible to remove the noise due to interference light on the mismatching subdivided image pickup surface from the plurality of radioactive ray sources.

Although the noise due to the interference light can be stopped by shifting the shining time of the plurality of radioactive rays, shining has to be switched at such a speed that the motion of the object is not perceptible in that case. As an application of that case, the object is not an animal but desirably an object at rest such as baggage and manufactured goods.

In order to convert a plurality of subdivided striped or dotted mixed images of a permeated object through the lattice to plane images corresponding to the plurality of radioactive ray sources, a plurality of phosphors having different luminous colors are applied to the subdivided image pickup surface. Then a half mirror is used to separate the images with the plurality of luminous colors into sheets of images and further a color filter having the same color as the luminous color of the phosphor is used to obtain the plurality of plane images from the respective images. Subsequently, polarized glasses or optical means are employed for offering the plane images thus separated to individual left and right eyes, so that the stereoscopic image of the permeated object can be observed. In this case, use can be made of the plurality of phosphors whose luminous spectrums are not overlapped, for example, red and green phosphors.

In giving the stereoscopic display of the image of the permeated object, magnification in the longitudinal direction (plane direction) should preferably be equal to that in the depth direction so as to make the stereoscopic display natural. Otherwise, if the depth magnification differs with at least the position of the object, precise stereoscopic perception is not obtainable when the stereoscopic image is observed. In order to render the depth magnification constant without relying on the position of the object, it is necessary to use the above parameters only to establish a relation of substantially $\alpha L=P$. This represents a law of a distance of binocular eyes in taking a picture and observing the display, as will be discussed in greater detail later with regard to FIG. 6. When this relation is not established ($\beta \neq 1$), moreover, the longitudinal and depth magnifications can be equalized when the display is made by placing the object at a position of x, $x=\beta(D/\alpha-d)/(1-\beta)$ from the radioactive ray sources. When the condition of substantially $\alpha L=P$ is met, the longitudinal and depth magnifications can be equalized by setting up the position D of an observer's view point at $D=\alpha d$. If some means for designating the position of the observer is used like this, a precise, natural stereoscopic image can be observed Digital signal processing is generally employed now in an X-ray radiography and when it is applied to the pickup and display apparatus of a stereoscopic permeated image, sampling synchronized with the subdivided striped or dotted image pickup surface of the image pickup device may be the simplest way of implementing such signal processing. In this case, digital signals are separated in response to striped patterns alternately appearing so as to separate plane images deriving from the respective radioactive ray sources. In the case of sampling of the striped or dotted image pickup surface, sampling is most reliable in view of stopping noise when it is made at a point where the striped or dotted radioactive rays from the plurality of radioactive ray sources are not overlapped. By individually shining the plurality of radioactive ray sources after removing the object, the striped or dotted patterns on the image pickup surface formed then are detected so as to set up sampling time manually or automatically in such a way that the patterns are prevented from overlapping at the sampling point.

The stereoscopic image may be displayed through the aforesaid polarized glasses or a peeping stereoscope in which two separated images correspond to each eye. However, the striped or dotted patterns on the image pickup surface may be utilized and displayed directly and stereoscopically by means of a lenticular lens board, a fly's eye lens board, or a lattice stopping visible light, without the need for polarized glasses or a stereoscope. The pitch of the lenticular lens, the fly's eye lens or the lattice is arranged so that striped or dotted sets formed on the surface of the pickup image are accommodated. The set in this case means two striped patterns if there are two radioactive ray sources. With this arrangement, the pattern formed on the image pickup surface is directly displayed on a picture tube or a projection screen so that the stereoscopic display may be made by only equipping it with the lenticular lens board, the fly's eye lens board, or the lattice plate.

A description has been given of the present invention in the form of the image pickup surface as a surface of an image intensifier or a surface to which a phosphor is applied. It is, however, acceptable to provide, as an image pickup device, a longitudinally-disposed line sensor. The lattice according to the present invention may be a longitudinally-long structure which allows only the radioactive rays incident on the line sensor, whereby the image of the whole permeated object can be obtained in the form of subsequent signals by moving the object or the line sensor and the lattice as an integral body in the longitudinal direction. Such a line sensor may be applied, by way of example, to cases where baggage is checked at airports, where the images of manufactured goods are checked or where stereoscopic image facsimiles are employed for telecommunication systems.

DETAILED DESCRIPTION

A detailed description will subsequently be given of an embodiment of the present invention.

Embodiment 1

Figure 1:
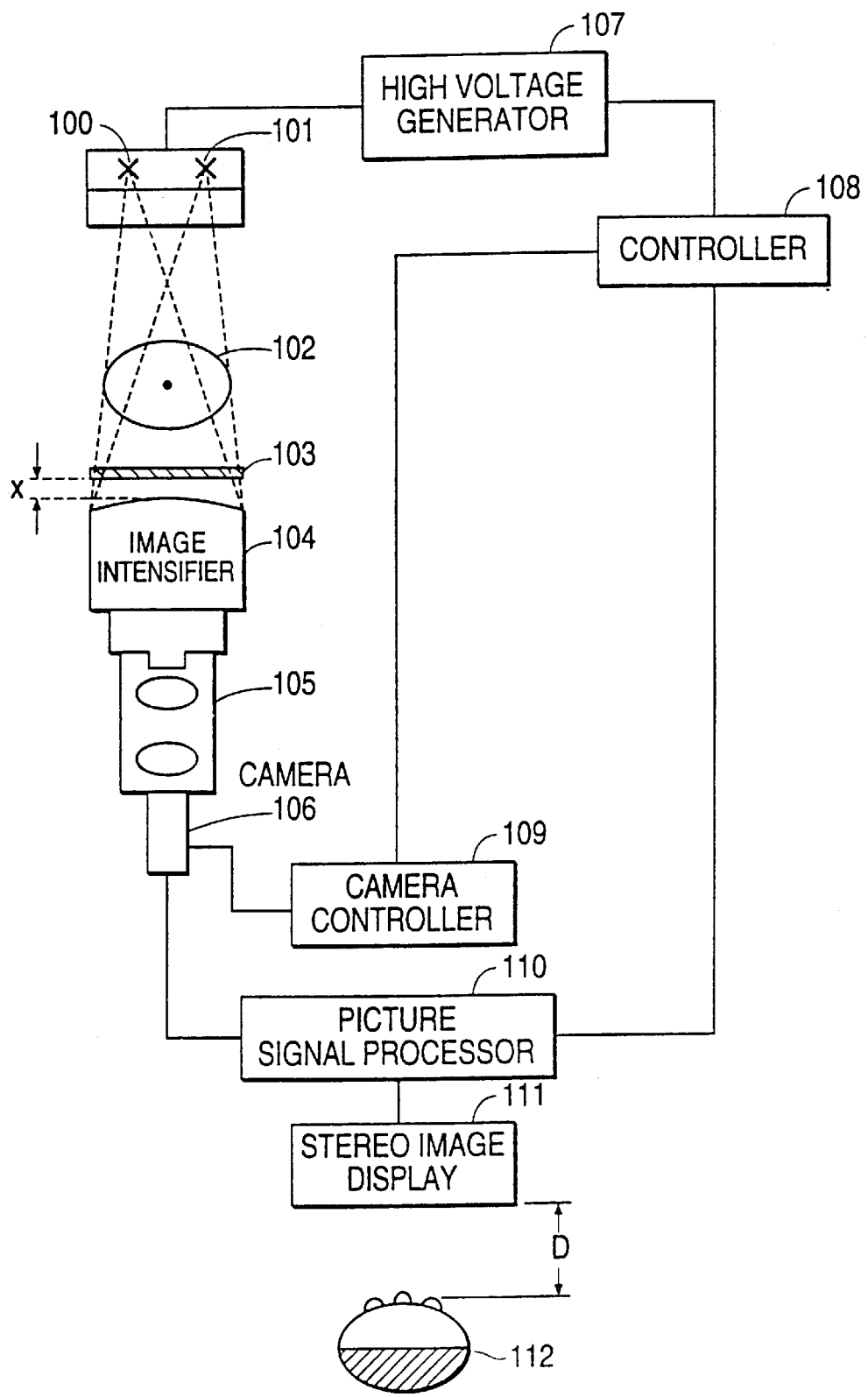
FIG. 1 is a structural diagram of an X-ray radiography according to a first embodiment of the invention.
Figure 2:
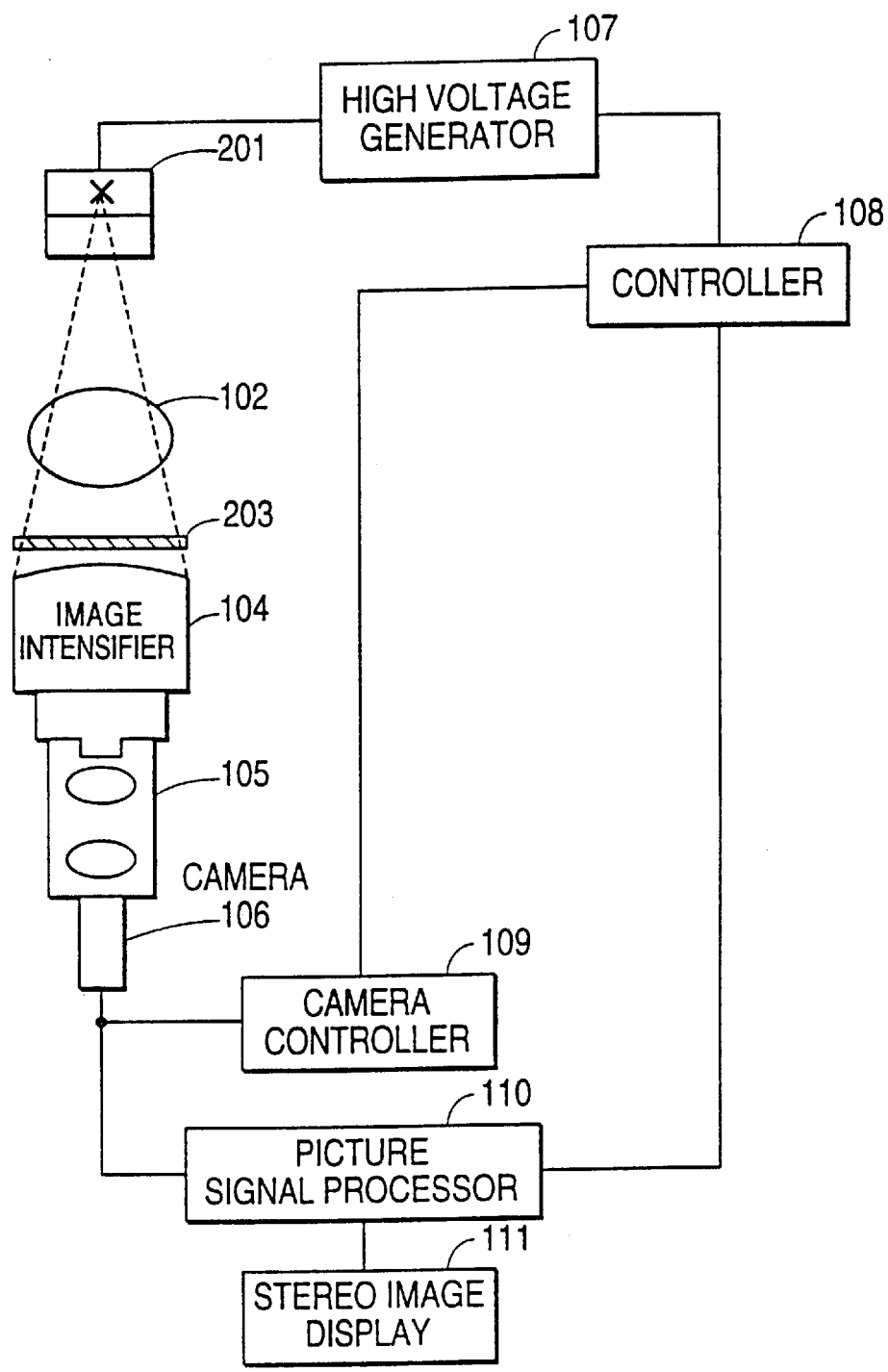
FIG. 2 is a structural diagram of a conventional X-ray radiography system.
Figure 3:
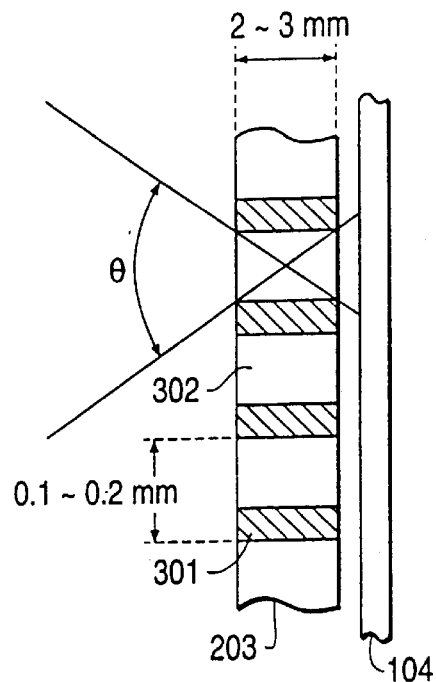
FIG. 3 is a diagram illustrating the construction and operation of a stopping sheet for a scattered radioactive ray for use in the conventional X-ray radiography system of FIG. 2.

Referring to FIGS. 1, 4 to 9 inclusive, a description will be given of an exemplary application of the present invention to an X-ray radiography according to the first embodiment thereof. FIG. 1 shows the construction of the apparatus, including two X-ray sources 100, 101 arranged 63 mm apart, the distance of which is equivalent to that of human binocular eyes; an image intensifier (I. I.) 104 employed as the image pickup surface of an image pickup device and placed 2 m apart from the X-ray sources 100, 101; a striped lattice 103 placed 2 mm apart from the front of the I. I. 104; a camera 106 in the rear of the I. I. 104 via an optical lens system 105; a camera controller 109 and a picture signal processor 110, both being connected to the camera 106; a stereoscopic image display 111 connected to the picture signal processor 110; a controller 108 of taking pictures connected to the camera controller 109 and the picture signal processor 110; and a high voltage generator 107 connected to the two X-ray generators 100, 101.

The operation of the apparatus shown in FIG. 1 will subsequently be described. An object 102 is situated in front of the striped lattice 103 in a manner such that the object almost contacts the lattice. Two pairs of X rays which are non-parallel with each other are simultaneously applied from the two X-ray sources 100, 101 to the object 102. The object in this case is typically a diseased part of the human body. The pairs of X rays that have permeated through the object 102 are incident on the striped lattice 103 and radiated therefrom in such a state that they are spatially divided into a plurality of partial permeating X rays before being incident on the I. I. 104. Two striped images of the permeated object respectively corresponding to the X-ray sources 100, 101 are formed on the surface (hereinafter called the image pickup surface) of the I. I. 104 in such a way that their partial X rays alternately appear. These images of the permeated object are released from I. I. 104 after being subjected to conversion to visible light and light amplification. The visible light is incident on the camera 106 via the optical lens system 105 and is converted into electrical signals to become image signals therein. The image signal is supplied to the picture signal processor 110 where the edges are emphasized and where the background noise is removed, and then to the stereoscopic image display 111. The images of the permeated object are thus stereoscopically displayed.

The controller 108 of taking pictures sends signals for controlling the generation of X rays to the high voltage generator 107 so as to drive the X-ray sources 100, 101 at high voltages. The controller 108 of taking pictures further sends timing signals to the camera controller 109 and the picture signal processor 110 to control the synchronization of the camera 106 with the picture signal processor 110. The picture signal processor 110 processes image signals from the camera 106 in synchronization with the scan of the camera 106.

An observer 112 observes stereoscopic images of the permeated object in accordance with the display method of a stereoscopic image at a distance of D, for example, 50 cm, from the stereoscopic image display 111. The observer may use polarized or anaglyphic glasses in accordance with the display method of a stereoscopic image.

Figure 4:
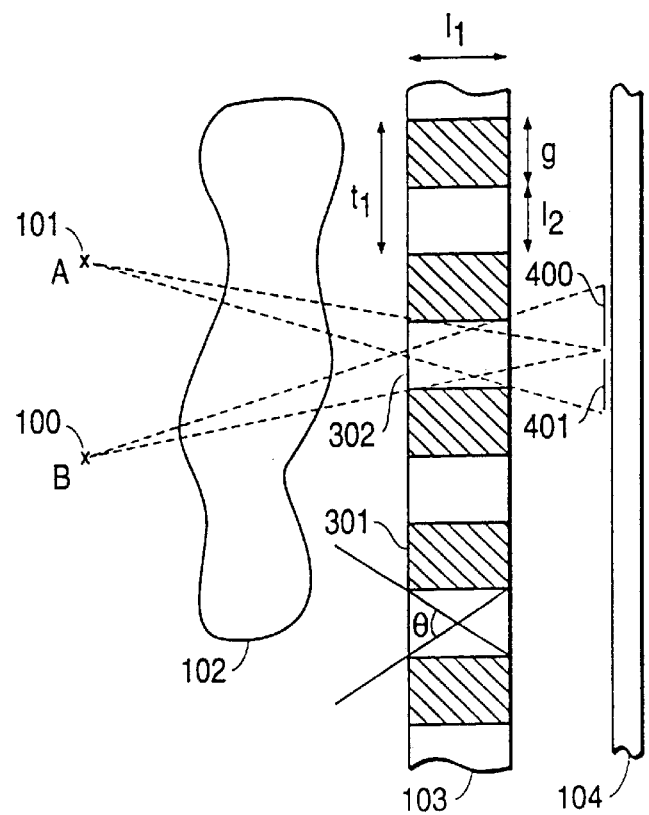
FIG. 4 is a diagram illustrating the construction and operation of a lattice according to the first embodiment of the invention.

Referring to FIG. 4, a description will now be given of the condition of arranging the X-ray sources with respect to the striped lattice 103 to generate two striped images 400 and 401. The striped lattice 103 is of one sheet construction in which lead portions 301 and aluminum permeable medium portions 302 (hereinafter called the window(s)) through which the rays pass) are disposed alternately and periodically. The periodic pitch $t_1$ is set at about 0.2 mm, the thickness $l_1$ of the lattice at about 2 mm and the size $l_2$ of the window through which the rays pass at about 0.1 mm.

In this lattice structure, the view field angle θ (at which the X rays in front of the lattice are allowed to pass therethrough) of the lattice is 2 arctan ($l_2/l_1$). In a case where $l_1$=2 mm, $l_2$=0.1 mm, and the pitch of the lattice $t_1$=0.2 mm, for example, the view field angle of the lattice will be 5.7°. Moreover, the X-ray sources have to be located within the range of view field angles. It is therefore needed to set the distance between the X-ray sources A101, B100 to not greater than 20 cm to ensure that the two X-ray sources remain within a view field angle of 5.7° as noted previously in a case where the distance from the X-ray source, which comprises the X-ray sources A101, B100, up to the striped lattice 103 is 2 m.

The two pairs of X rays radiated from the X-ray sources A101, B100 within the view field angle and permeated through the object 102 pass through the window 302 of the striped lattice 103 and then proceed further up to a point at which they are set free from overlapping. The image pickup surface of the I. I. 104 is arranged at that position, so that the X rays that permeate the object are spatially separated to make individual images on the surface of the I. I. 104.

Figure 5:
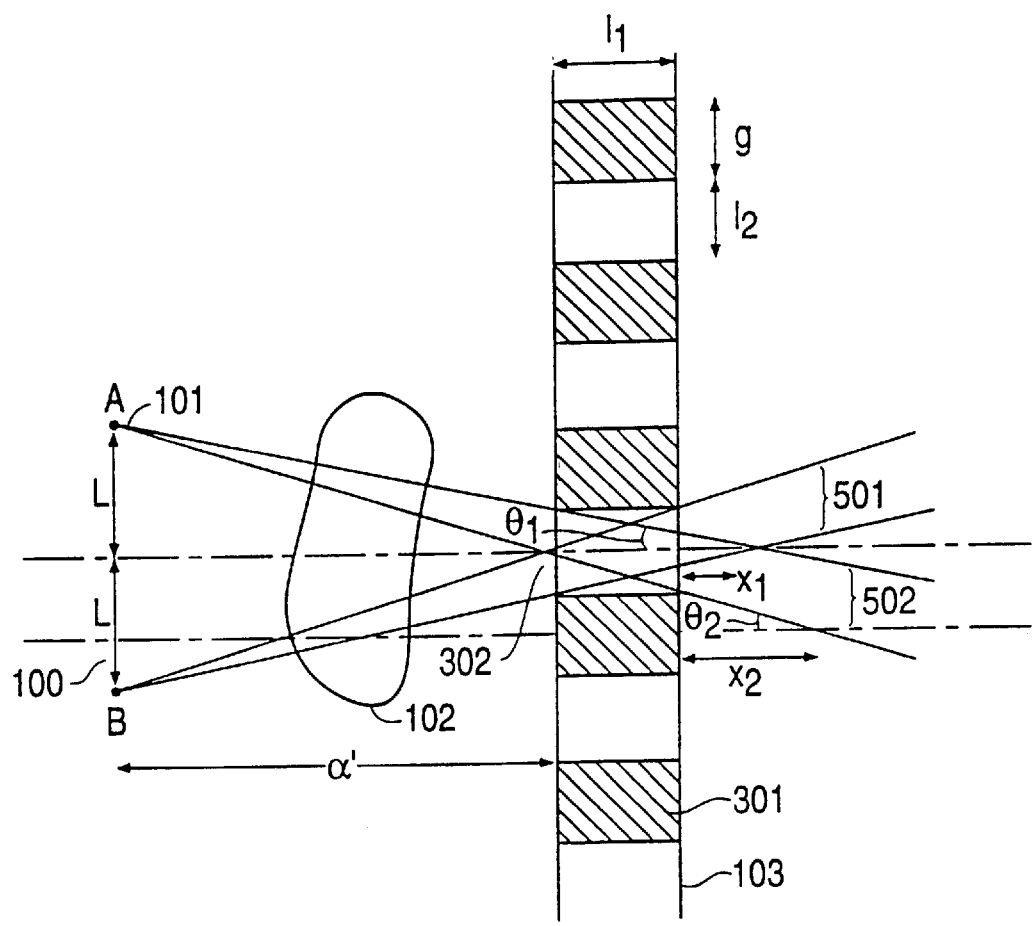
FIG. 5 is a diagram illustrating the setting up of the length of a lead lattice according to the first embodiment of the invention.

Referring to FIG. 5, a description will now be given of the way of obtaining the position of the picked up images on the surface of the I. I. 104. First, two kinds of distances $x_1$, $x_2$ are obtained: the distance $x_1$ from the radiation surface of the striped lattice 103 up to the position where the spatial areas 501, 502 of the pairs of permeating X rays passed through the window 302 of the striped lattice 103 become free from overlapping; and the distance $x_2$ from the radiation surface of the striped lattice 103 up to a position where spatial areas 501, 502 widen up to half the length g of the lead portion 301 of the striped lattice 103 (the position where the spatial area is beginning to overlap the spatial area of another adjacent picture element).

Given the length of the striped lattice 103 in the thickness direction=$l_1$, the length of the lead portion 301=g, the length of the window through which the rays pass=$l_2$, the distance between two X-ray sources=2L, distance from the two X-ray sources up to the surface of the striped lattice 103 =d', the incident angle (incident on a right angle) of the permeating X ray incident on the end of the window 302 of the striped lattice 103=$θ_1$, and the incident angle of the permeating X ray that has radiated from the end of the window 302=$θ_2$, $$\tan θ_1 = L/(d'+l_1+x_1) = l_2/2(l_1+x_1) \quad (1)$$

$$\tan θ_2 = (L+l_2/2+g/2)/(d'+l_1+x_2) = g/2x_2 \quad (2)$$

are obtained. By solving $x_1$ and $x_2$ using Eqs. (1) and (2), $$x_1 = (l_2(d'+l_1) - 2Ll_1)/(2L-l_2) \quad (3)$$

$$x_2 = g(d'+l_1)/(2L+l_2) \quad (4)$$

are obtained.

Given that the position of the images on the image pickup surface of the I. I. 104 is expressed by the distance S from the radiation surface of the striped lattice 103, the condition under which the permeating X rays are spatially separated is $$s \geq x_1 \text{ and } s \leq x_2 \text{ (that is, } x_1 \leq s \leq x_2) \quad (5)$$

Therefore, $x_1 < x_2$.

When this equation is rearranged by substituting Eqs. (3), (4), $$(2L+l_2)\{l_2(d'+l_1)-2Ll_1\}/(2L-l_2)(d'+l_1) \leq g \quad (6)$$

the relation above is obtained.

Given L=31.5 mm, $l_1$=2 mm, $l_2$=0.1 mm, d'=2 m, the length g of the lead portion 201 has to be set at not less than 0.037 mm in view of this relation. When the value g is set at 0.037 mm, moreover, $x_1$, $x_2$ are as follows: $x_1$=1.17 mm and $x_2$=3.17 mm. As a result, the image pickup surface of the I. I. 104 needs to be located apart from the radiation surface of the striped lattice 103 within the range of 1.17 mm to 3.17 mm.

Figure 6A:
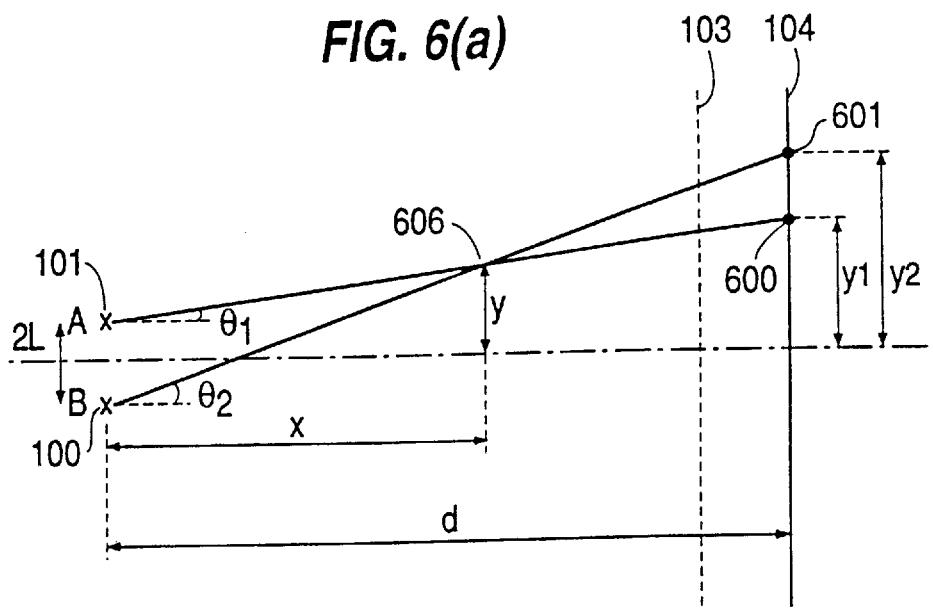
FIGS. 6(a) and 6(b) are diagrams illustrating the distortion of a stereoscopic image according to the first embodiment of the invention.
Figure 6B:
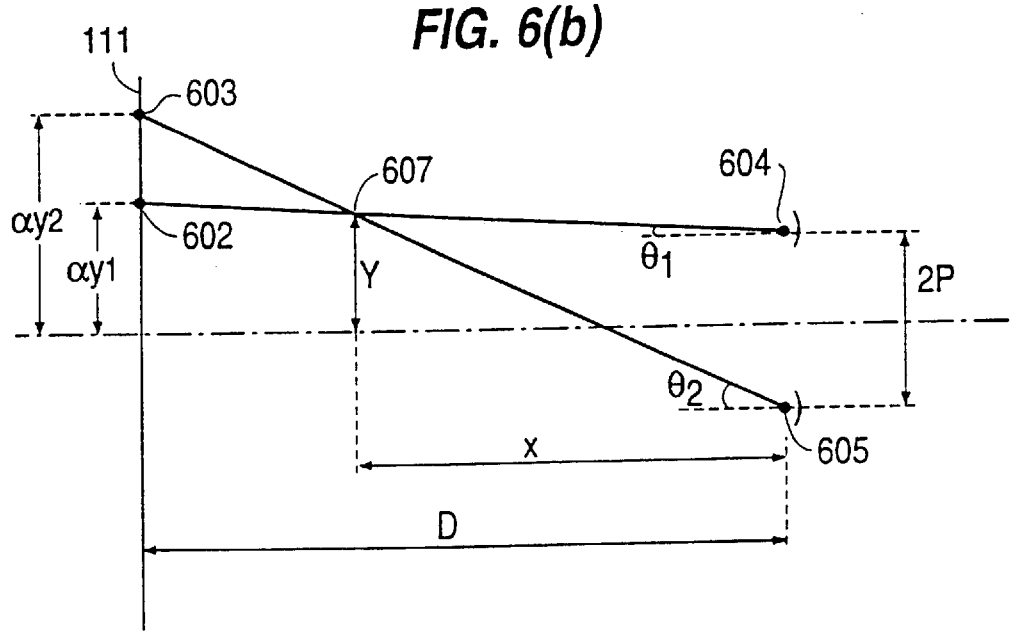

Referring to FIGS. 6(*a*) and 6(*b*), a description will now be given of the prevention of distortion of the stereoscopic image. In order to prevent the stereoscopic image from being distorted, the longitudinal and depth magnifications are set equal when the stereoscopic image is displayed.

FIG. 6(*a*) refers to the positioning of a picked-up image. The X-ray sources A101, B100 are arranged 2L apart and also distanced by d from the surface of the picked-up image on the surface of the I. I. 104. A point object 606 as the point 1 of the object is distanced by x from the center point between the X-ray sources A101, B100 along the center line, and set y apart from the center line. In this case, the formation of the image of the point object 606 is made by the X-ray source A101 at a point 600 which is $y_1$ apart from the center line on the image pickup surface of the I. I., whereas the formation of the image of the point object 606 is made by the X-ray source B100 at a point 601 which is $y_2$ apart from the center line on the surface thereof. From the geometric relations shown in FIG. 6(*a*), the following are obtained:

$$\tan \theta_1 = (y_1-L)/d = (y-L)/x \quad (7)$$

$$\tan \theta_2 = (y_2+L)/d = (y+L)/x \quad (8)$$

FIG. 6(*b*) shows a display arrangement. On the display screen 111 are points 602, 603 as the respective points 600, 601 making images on the image pickup surface of FIG. 6(*a*). The distances of the points 602, 603 from the center line are respectively multiplied by $\alpha$ with respect to the points 600, 601 to define them as $\alpha y_1$, $\alpha y_2$. In this case, $\alpha$ signifies a picture magnification on the display screen with respect to the image pickup surface. Now assuming the observer observes the point 602 with his right eye 604, D apart from the display screen 111 and the point 603 with his left eye 605 likewise, there develops a convergence angle in the binocular eyes. Consequently, one point may be observed as if the point is distanced by X from the observer along the center line and positioned Y apart from the center line (i.e., at a display point 607). Given that 2P represents a distance of binocular eyes (P=distance from the center line up to the eye), the following relations are established:

$$\tan \theta_1 = (\alpha y_1 - P)/D = (Y-P)/X \quad (9)$$

$$\tan \theta_2 = (\alpha y_2 + P)/D = (Y+P)/X \quad (10)$$

When $y_1$, $y_2$ are eliminated from Eqs. (6), (7), (8), (9), $$\alpha L\{(-d/x)+l\} = P\{(-D/X)+l\} \quad (11)$$

$$dLY-(L-P/\alpha)xY-dPy-0 \quad (12)$$

are obtained.

Eq. (11) is differentiated to obtain depth magnification $((dX)/(dx))$. Then $$(dX)/(dx) = \beta dD/\{\beta d+(l-\beta)x\}^2 \quad (13)$$

is obtained. However, $$\beta = \alpha L/P \quad (14)$$

Moreover, Eq. (12) is differentiated to obtain longitudinal magnification $((dY)/(dy))$. Then $$(dY)/(dy) = \alpha d/\{\beta d+(l-\beta)x\} \quad (15)$$

is obtained. Here, (dx)=0 to obtain the displacement quantity in the direction of Y on the part of the observer when the point object 606 undergoes a minute quantity (dy) of displacement in only the direction of y.

From Eqs. (13) and (15), $\beta$=1 is essential to make the depth and longitudinal magnifications constant, irrespective of the position of the point object. In other words, $\alpha L = P$ is justified. Given $\alpha$=0.5, P=31.5 mm, the distance 2L between the two X-ray sources may be set at 126 mm.

The depth magnification then turns out to be D/d from Eq. (13) and the longitudinal magnification to be $\alpha$ from Eq. (15). In a case where $\alpha L = P(\beta=1)$, the depth and longitudinal magnifications become equal when D=$\alpha$d. Given $\alpha$=0.5, d=2 m, for example, the distance from the observer may be set at 1 m.

More specifically, the depth and longitudinal magnifications are equalized to allow the observer to observe a natural stereoscopic image when some measures are taken to define the position D of the observer's view point by, for example, setting up the head's position or designating the seat position so as to justify D=$\alpha$d.

When $\beta \neq 1$, that is, $\alpha L \neq P$, the object may be positioned at $$x = \beta\{(D/\alpha)-d\}/(l-\beta) \quad (16)$$

from Eqs. (13) and (15) to equalize the depth and longitudinal magnifications. Given $\beta$=0.5, $\alpha$=0.5, D=1.5 m, and d=2 m, for example, the position x of the object may be set to 1 m. While the object is placed at the position given by Eq. (16) for images to be picked up, the observer is to observe the images at a position D (1.5 m) apart from the display screen. A natural stereoscopic image in which the depth and longitudinal magnifications are equal can thus be observed.

Figure 7A:
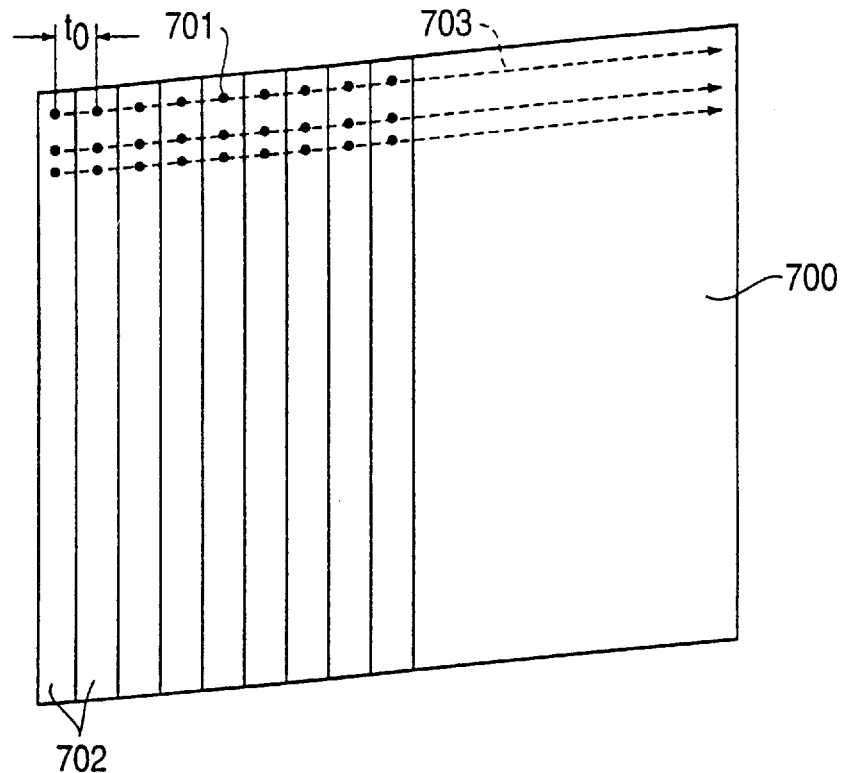
FIGS. 7(a), 7(b) and 7(c) are diagrams illustrating a sampling method when the image is converted into digital signals according to the first embodiment of the invention.
Figure 7B:
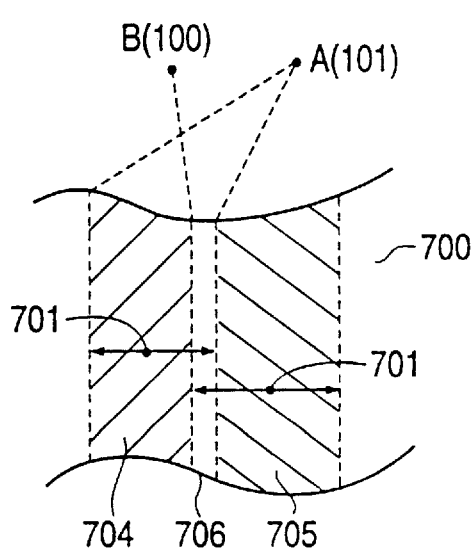

Digital signal processing can be employed for a method of image processing according to an aspect of the invention. Referring to FIGS. 7(*a*) to 7(*c*), a description will now be given of a sampling method for use when a visible light image on the back surface of the I. I. 104 is converted into digital signals. Striped images 702 are made on the back surface 700 of the I. I. 104. As shown in FIG. 7(*a*), these images are subjected to progressive horizontal scanning 703 by means of the camera 106 to obtain analog signals. The analog signals are sampled at predetermined time intervals. Given that the period $t_0$ of the sampling position is made equal to the pitch $t_1$ (e.g., 0.2 mm) of the striped lattice 103 and that the spatial scanning velocity is set at y (e.g., 40 cm/50 µs=8β×10³/sec), the sampling time period will be $t_0/v$ (e.g., 5 nsec).

The sampling position is set up before the object 102 is installed. First, X rays are emitted from each X-ray source to obtain each striped image 702 formed on the back surface 700 of the I. I. Consequently, the striped images 702 deriving from both X-ray sources may be overlapped slightly. In other words, striped images 704, 706 deriving from the X-ray source A101 and those 705, 706 from the X-ray source B100 may be overlapped in the area 706 shown in FIG. 7(b). In this case, sampling positions 701 are set up in the respective areas 704, 705 free from overlapping. Such a sampling position may needless to say be set up at any position of the striped image on condition that the striped images 702 deriving from both the X-ray sources are not overlapped.

Figure 7C:
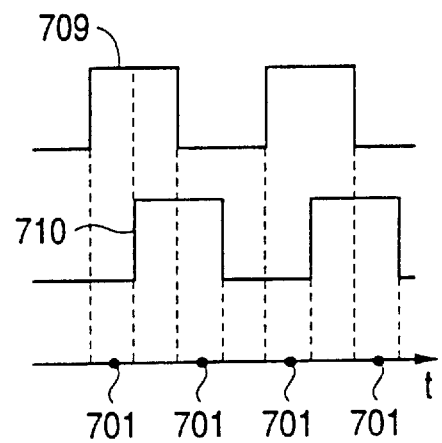

Subsequently, the sampling position in the form of sampling time is stored in the picture signal processor 110. Referring to a case where the images 702 deriving from both X-ray sources are slightly overlapped, a description will be given of the way of setting up the sampling time by way of example. As shown in FIG. 7(c), rectangle waves 709 are obtained by scanning the back surface 700 of the I. I. 104 by means of the x-ray source A101, whereas rectangle waves 710 are obtained by scanning the back surface 700 of the I. I. 104 by the X-ray source B100. Both the rectangle waves 709 and 710 are overlapped because their phases are shifted. The sampling time 701 is set up in the portion where the rectangle waves are not overlapped.

When the X-ray sources A101, B100 are placed close to the striped lattice 103, moreover, the pitch of the striped image 702 formed in the center part of the back surface 700 of the I. I. differs from the pitch of what is formed in the peripheral part thereof. In this case, the sampling time is not set at equal intervals but required to be corrected in agreement with the shifting of the pitch of the striped image 702.

Figure 8A:
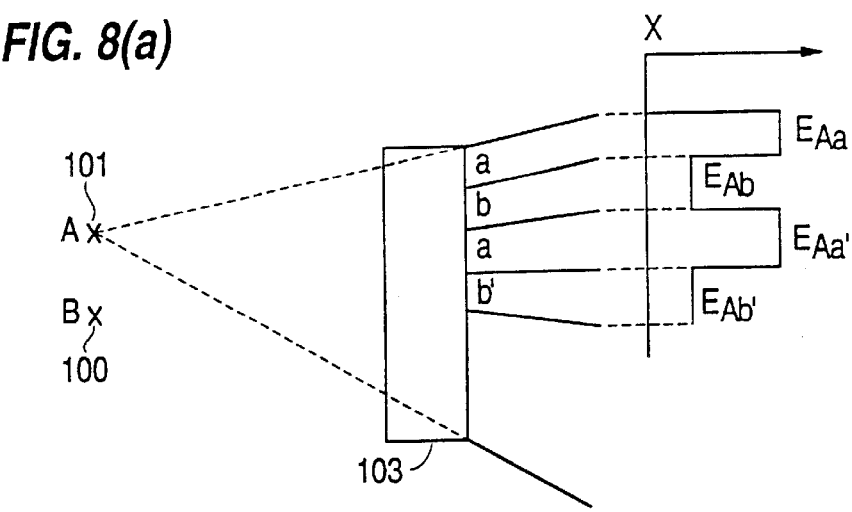
FIGS. 8(a), 8(b) and 8(c) are diagrams illustrating the method of reducing image cross talk from a permeated object according to the first embodiment of the invention.
Figure 8B:
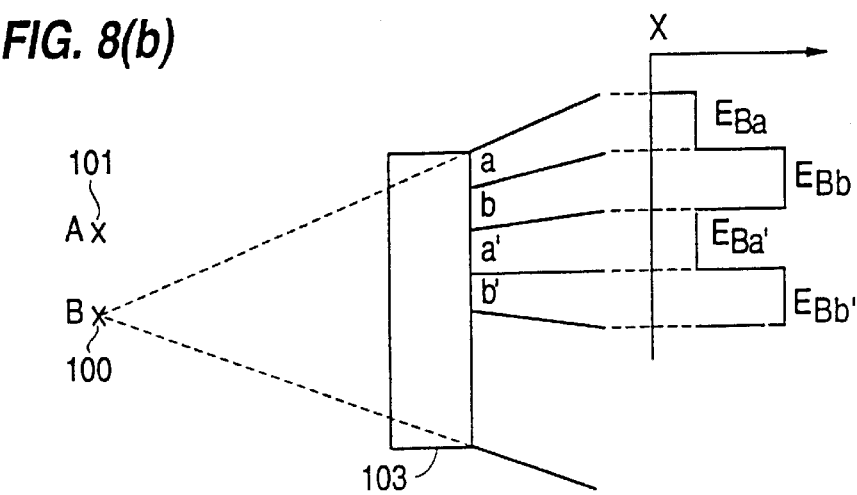
Figure 8C:
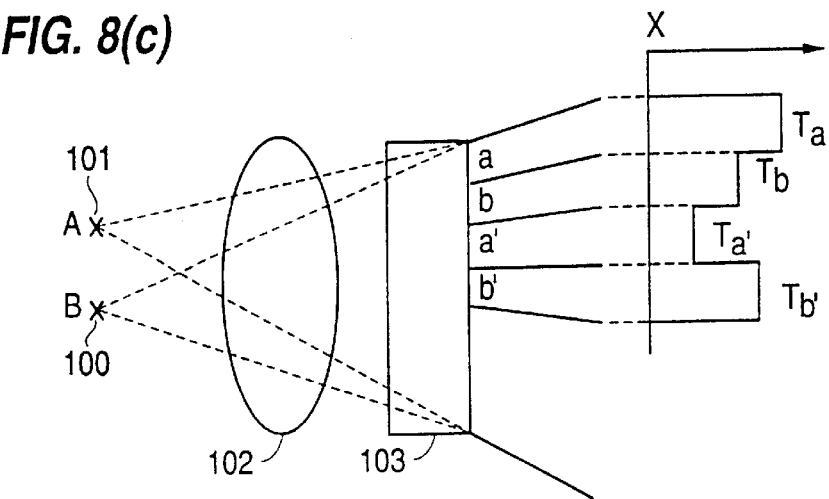

Referring to FIGS. 8(a) to 8(c), a description will now be given of the method of reducing the cross talk generated on the image pickup surface of the I. I. 104 with the images of the permeated object deriving from different X-ray sources.

FIG. 8(a) shows X-ray intensity on the image pickup surface when the striped lattice 103 is irradiated with X rays from only the X-ray source A (101) without the presence of the object. FIG. 8(b) shows X-ray intensity on the image pickup surface when the striped lattice 103 is irradiated with X rays from only the X-ray source B (100) without the presence of the object. In FIGS. 8(a), 8(b), a, a', . . . represent divided spaces when the X rays from the X-ray source A (101) pass through the striped lattice 103 in an ideal mode, and b, b' divided spaces when the X rays from the X-ray source B (100) pass therethrough in an ideal mode likewise. E represents X ray intensity, and substripts denote X-ray intensity in a specific space. For example, $E_{Aa}$ signifies X-ray intensity in the space a when the X ray is radiated from the X-ray source A.

It is natural for X rays having X-ray intensity $E_{Aa}$, $E_{Aa'}$, . . . to be detected in the spaces a, a', . . . corresponding to the X-ray source A101. If, however, X rays (leak X rays)) having X-ray intensity $E_{Ab}$, $E_{Ab'}$, . . . are detected in the spaces b, b' . . . which do not correspond to the X-ray source A101, it also means that the X rays are not being radiated in an ideal mode. Although the intensity $E_{Ab}$, $E_{Ab'}$, . . . of the leak X rays are desirably reduced to zero, they exist to some degree, depending on the position of the X-ray source and the resolution of dividing X rays of the striped lattice 103. The same will apply to FIG. 8(b).

Subsequently, an object is actually placed in the path of the X-rays as shown in FIG. 8(c). $T_a$, $T_b$, $T_{a'}$, $T_{b'}$ in FIG. 8(c) show X-ray intensity in the spaces a, b, a', b' when the X-ray sources A 101, B100 are simultaneously caused to radiate X rays.

In this case, leakage X-ray intensity deriving from the X-ray source B is added to the original X-ray intensity $T_a$ deriving from the X-ray source A 101, and cross talk is caused. The leakage X-ray intensity can be obtained by an approximate value ($T_b \cdot E_{Ba}/E_{Bb}$). At this time, $E_{Ba}/E_{Bb}$ shows a noise ratio in the space b when only the X-ray source B is operated.

By correcting the X-ray intensity in the space a to ($T_a - T_b \cdot E_{Ba}/E_{Bb}$), the cross talk with the leakage X ray deriving from the X-ray source B can be reduced. By correcting the X-ray intensity in the space b to ($T_b - T_a \cdot E_{Ab}/E_{Aa}$) likewise, the cross talk with the leakage X ray deriving from the X-ray source A can be reduced. These two kinds of correction are similarly applied to the other spaces a', b'. Such correction can be effected by taking the visible light image on the back surface of the I. I. 104 corresponding to the X-ray intensity in the state of FIG. 8(a) to 8(c) by means of the camera 106, and calculating the result in the normal technique within the picture signal processor 110. Cross talk with the leakage X ray is also reducible in the same way even when there are more than two X-ray sources.

Figure 9:
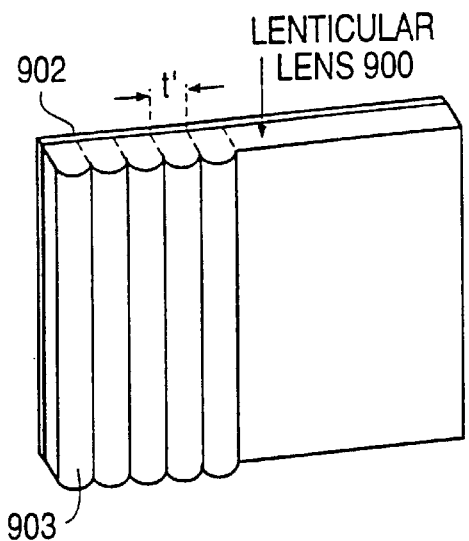
FIG. 9 is block diagram of a stereoscopic image display according to the first embodiment of the invention.

Referring to FIG. 9, a description will now be given of an arrangement that can be used for the stereoscopic image display 111 (see FIG. 1). A projection display is employed as a display 902 and a lenticular lens board 900 is fitted to the surface of a screen. A plurality of lenses 903 similar to half cylinders are horizontally arranged on the lenticular lens board 900. The horizontal length t' of the lens 903 like a half cylinder relies on the period $t_0$ at the sampling position of the striped image 702 on the back surface of the I. I. 104. In other words, since the images of the permeated object from the two X-ray sources are separated by binocular eyes when there are two X-ray sources, only the visible light resulting from converting the digital signals given by two adjoining sampling positions in the display 902 needs accommodating within one half-cylinder-like lens 903. In this case, the observer is able to observe a stereoscopic image with the naked eyes without using polarized glasses. On the other hand, a liquid crystal or a cathode-ray tube in place of the projection display may be used as the display 902.

Although a description has been give of a case where X rays are caused to shine on the object according to this aspect of the invention, not only such X rays but also other radioactive rays may be used to achieve the same effect.

Embodiment 2

Figure 10:
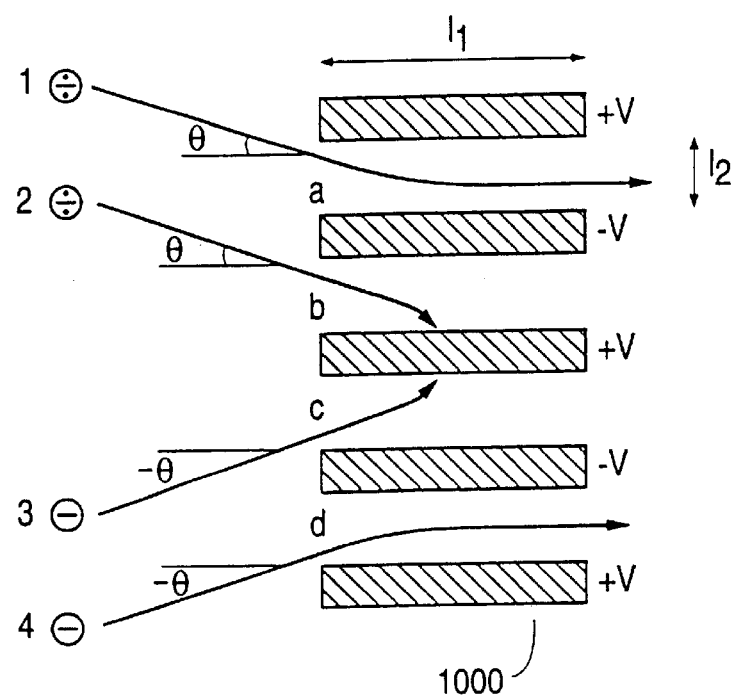
FIG. 10 is a block diagram of a lattice according to a second embodiment of the invention.
Figure 11A:
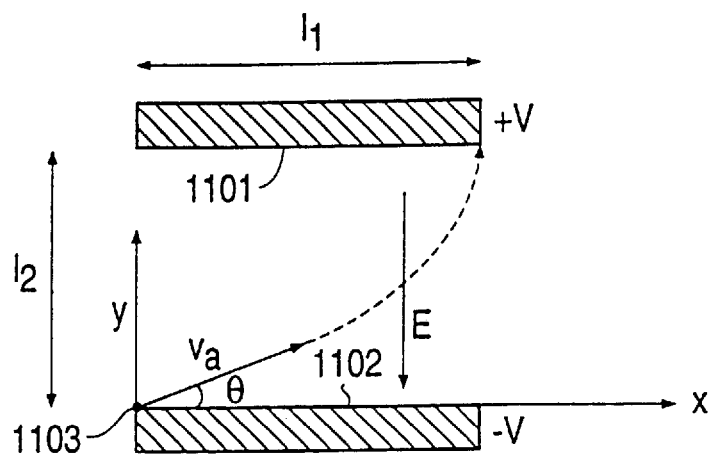
FIGS. 11(a) and 11(b) are diagrams illustrating the setting up voltage to be supplied to electrodes of the lattice according to the second embodiment of the invention.
Figure 11B:
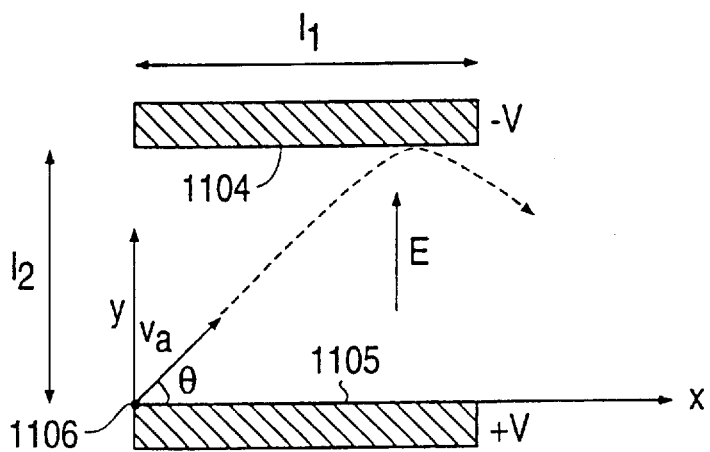

Referring to FIGS. 10, 11(a) and 11(b), a description will now be given of lattices effective for particle rays having an electric charge, for example, electrons as radioactive rays according to the second embodiment of the invention. Electrons are employed by way of example in the following discussion.

FIG. 10 illustrates an incident status where electrons are incident on a lattice. A voltage of +V (>0, e.g., 8 kV) and a voltage of -V (e.g., -8 kV) have been applied to odd and even number lattice boards 1000. Two permeating electron beams are incident on the lattice boards 1000 at incident angles of θ (e.g., 5°) and -θ (e.g., -5°), respectively. The electric field is directed downward in a window a as viewed from FIG. 10 and consequently an electron beam 1 incident on the window a at an angle of θ passes therethrough while receiving the force directed upward because the electron charge is -e (e>0, e=1.602÷10$^{19}$ C). On the other hand, the electric field is directed upward in a window b as viewed from FIG. 10 and consequently an electron bean 2 incident on the window b at an angle of θ passes therein while receiving the force directed downward. However, the electron beams 2 is absorbed by an electrode without being passed through the window b since its incident angle has been directed downward as viewed from FIG. 10.

Electron beams 3, 4 incident at an angle of −θ follow the same principle as noted previously likewise and the electron beam 3 is absorbed by the electrode even though it is incident on a window c, whereas the electron beam 4 passes through a window d. In other words, the electron beams incident at an angle of θ pass through the window whose electric field is directed downward only as viewed from FIG. 10, whereas the electron beams incident at an angle of −θ pass through the window whose electric field is directed upward only as viewed therefrom. Therefore, the lattice boards to which different voltages have been applied are used to spatially separate electron beams different in their incident angles.

Thus, the image pickup surface is so arranged as to stick to the back sides of the lattice boards 1000 since the permeation and stopping of electron beams are controllable in the windows of the lattice to which voltages have been applied.

FIGS. 11(a), 11(b) show the conditions of setting up voltages V across electrodes for controlling the passage of electrons through electrode lattices and the stopping of their passage therethrough.

FIG. 11(a) refers to the method of stopping electron beams, wherein voltages of +V (V>0) and −V are applied to electrodes 1101, 1102 respectively. An incident point 1103 is set at the origin of coordinates, and x and y are taken on the axes of abscissa and ordinate. From the origin 1103, electrons are incident on an incident window at a velocity of va (e.g., va=0.7×10$^8$ m/sec) and an angle of θ (e.g., 5°). The electrons are charged at −e(e>0, e=1.602×10$^{-19}$ C) and assuming their mass is m (m=9.109×10$^{-31}$ kg), they receive the force directed upward as the electric field is directed downward as viewed from FIG. 11 and absorbed by the electrode 1101.

Next, the condition of setting up the voltage V at which the electrons are absorbed by the electrode will be discussed. Given the length of the electrode in the thickness direction= $l_1$ (e.g., 0.5 mm), and the length of the window through which the rays pass= $l_2$ (e.g., 2 mm), the electron motion equation is given by $$d^2x/dt^2=0 \tag{17}$$

$$d^2y/dt^2=-eE/m=2\ eV/(ml_2) \tag{18}$$

The coordinates and velocity of the electron at t=0 are then given as the initial conditions.

$$dx/dt(t=0)=va\ \sin\theta \tag{19}$$

$$dy/dt(t=0)=va\ \cos\theta \tag{20}$$

$$x(t=0)=0 \tag{21}$$

$$y(t=0)=0 \tag{22}$$

By solving Eqs. (17), (18) using the initial condition, $$x=tva\ \sin\theta \tag{23}$$

$$y=t^2\ eV/(ml_2)+tva\ \cos\theta \tag{24}$$

If the position y of the electron passing to cover the distance $l_1$ equivalent to the length of the window of the lattice is greater than the length $l_2$, the electron is absorbed by the electrode 1101.

$$l_1=t_0 va\ \sin\theta \tag{25}$$

$$Y(t_0)>l_2 \tag{26}$$

From Eqs. (24), (25), (26), the setting range of voltages V at which the electrons are absorbed by the lattice boards and stopped in the window is given by $$V>ml_2\ va^2\ \sin^2\theta(l_2-l_1\cot\theta)/(el_1^2) \tag{27}$$

Given, for example, $l_1$=0.5 mm, $l_2$=2 mm, va=0.7×10$^8$ m/sec, θ=5°, e=1.602×10$^{-19}$ C, and m=9.109×10$^{-31}$ kg, the result will be V>−6.29×10$^5$V and since V>0, the condition of Eq. (27) is automatically satisfied in this example.

Referring to FIG. 11(b), the passing condition of electrons is subsequently obtained. Coordinate axes are taken as in FIG. 11(a). From the origin of the coordinates, electrons are incident on the window at an incident angle of θ and an incident velocity of va. Voltages of −V (V>0) and +V are applied to upper and lower electrodes 1104, 1105, respectively. At this time, an electric field E in the window through which the rays pass is directed downward. The coordinates and velocity of the electron are as follows:

$$x=tva\ \sin\theta \tag{28}$$

$$y=-t^2\ eV/(ml_2)+tva\ \cos\theta \tag{29}$$

$$dx/dt=va\sin\theta \tag{30}$$

$$dy/dt=-2\ teV/(ml_2)+tva\ \cos\theta \tag{31}$$

As the electrons receive force in the direction of −y, the velocity in the direction of y attenuates and when the velocity in that direction is reduced to 0, the electrons are stopped from colliding with the electrode 1104 on condition that the coordinate of y is not greater than $l_2$.

$$dy/dt(t=t')=0 \tag{32}$$

$$Y(t')<l_2 \tag{33}$$

From Eqs. (29), (31), (32), (33), the condition of setting up the voltage at which the electrons are prevented from colliding with the electrode 1104 is given by $$V>mva^2\ \cos^2\theta/(4e) \tag{34}$$

Given, for example, θ=5°, va=0.7×10$^8$ m/sec, e=1.602×10$^{-19}$ C, and m=9.109×10$^{-31}$ kg, the result will be V>6.9 kV.

As shown in FIG. 11(b), electron first approaches the upper electrode 1104 and is bounded, and then moves in the direction of the lower electrode 1105 again. The condition under which the electron is kept from being absorbed by the electrode 1105 is such that as the electron makes a parabolic movement in the window, the twofold length of time t' required for the electron to reach the top of the parabola is needed to be at least greater than the time $t_0$ required until it completely passes through the window.

$$2t'>t_0 \tag{35}$$

From Eqs. (15), (21), (22), (25), the condition of setting up V at which the electrons are allowed to pass through the window without being absorbed by the electrode 705 is given by $$V<ml_2 va^2\ \sin\theta\cos\theta/(el_1) \tag{36}$$

Given, for example, $l_1$=0.5 mm, $l_2$=2 mm, e=1.602÷10$^{19}$ C, m=9.109÷10$^{31}$ kg, va=0.7×10$^8$ m/sec, θ=5°, the result will be V>9.7 kV.

Therefore, the condition of setting up V at which the electrons are allowed to pass through the window is given by Eqs. (34), (36).

In this case, the right sides of Eqs. (27), (24) must be smaller than that of Eq. (26). Assuming now the ratio of the length of $l_1$ (e.g., 0.5 mm) to that of $l_2$ (e.g., 2 mm) is $\rho$ (e.g., $\rho=4$), ($\rho=l_2/l_1$) and $$(\text{¼}) \cot \theta < \rho < 2 \cot \theta \qquad (37)$$

is essential. When $\theta=5°$, for example, $2.86<\rho<22.8$.

With respect to the condition of setting up the voltage V at which the passage and stopping of electrons are controlled, what is greater than the right sides of Eqs. (17), (24) is made Vmin from Eqs. (27), (34), (36) and with Vmax as the right side value of Eq. (26), Vmin=Max[$ml_2va^2 \sin^2 \theta(l_2-l_1 \cot \theta)/(el_1^2)$, $mva^2 \cos^2 \theta/(4e)$](38)

Vmax=$ml_2va^2 \sin \theta \cos \theta/(el_1)$

Vmin<V<Vmax (39)

are obtained. Given, for example, $m=9.109\times10^{-31}$ kg, $e=1.602\times10^{-19}$ C, $va=0.7\times10^8$ m/sec, $l_1=0.5$ mm, $l_2=2$ mm, $\theta=50°$, the results will be Vmin=6.9 kV, Vmax=9.7 kV.

The electron beams having different angles are spatially divided by applying the voltage V given by Eq. (39) to the electrode.

Although a description has been given of radioactive rays as electron beams according to this aspect of the invention, this is, needless to say, applicable to all other charged particle rays having ions, for example. Although odd and even number voltages to be applied to the lattice are respectively defined as +V and -V, voltage having any voltage difference are obviously usable to bring about the same type of operation. Moreover, the incident angles of two electron beams are set at symmetrical angles $\theta$ and $-\theta$ because this is the best condition of resolution and it is also acceptable to employ two different angles for satisfying this condition.

Embodiment 3

Figure 12:
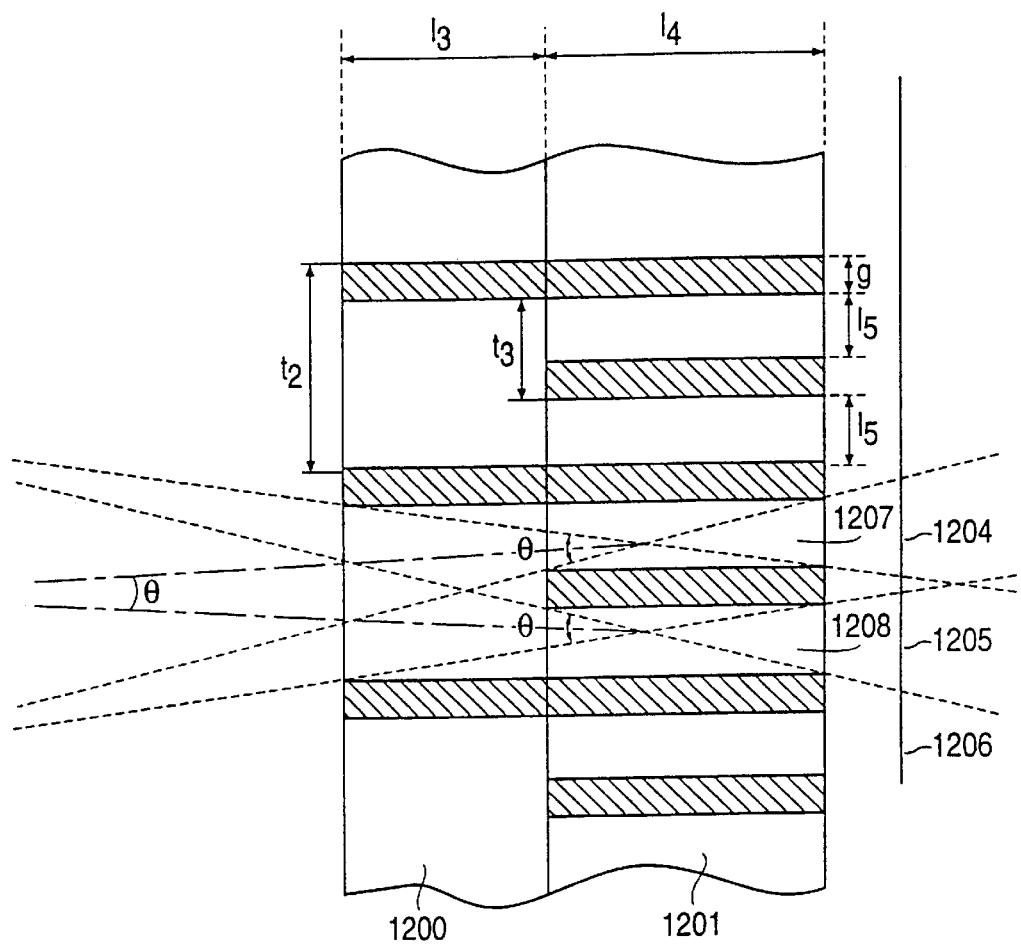
FIG. 12 is a block diagram of a lattice according to a third embodiment of the invention.

Referring to FIG. 12, a description will now be given of a lattice made by joining two sheets of lattice boards different in their pitches to let them have a plurality of directivities according to the third embodiment of the invention. In effect, the first lattice 1200 provides for an initial cutting down of the radioactive rays while the second lattice 1201 ensures that the images do not overlap.

More specifically, FIG. 12 shows a case where reference is made to the following items: $l_3$ (e.g., 2 mm) as the thickness of a lattice board 1200; $t_2$ (e.g., 0.4 mm) as the pitch of the lattice 1200; $l_4$ (e.g., 3 mm) as the thickness of a lattice board 1201; and $t_3$ (e.g., 0.2 mm) as the pitch of the lattice 1201. In this example, the pitch $t_2$ (0.4 mm) of the lattice 1200 is set just twice as great as the pitch $t_3$ (0.2 mm) of the lattice 1201 and $l_3<l_4$. As shown in FIG. 12, moreover, the window of the lattice board 1200 conforms to $t_2-(0.3$ mm) with $l_5$ (e. g., 0.1 mm) as the breadth of the window of the lattice board 1201 and g as the breadth of the lead portions of the lattice boards 1200, 1201. As also shown in FIG. 12, an object is placed to the left of the lattice board 1200 and the lattice pitch $t_2$ (0.4 mm) of the lattice board 1200 close to the object is set greater than the lattice pitch $t_3$ (0.2 mm) of the lattice board 1201 far from the object. In this case, the relation between the pitch of the lattice board 1200 and that of the lattice board 1201 is set to $mt_2=nt_3$ (m, n=integers, $m \leq n$). FIG. 12 shows an example of m=1, n=2.

In the case of FIG. 12, radioactive rays which pass through the window of the lattice board 1200 are separated in two windows 1207, 1208 of the lattice board 1201. The view field angles $\theta$ of the windows 1207, 1208 are obtained from simple geometric calculations: $\theta$ arctan ($l_5/l_4$+arctan ($l_5/(l_3+l_4)$). At this time, the angle $\theta$ formed by the center lines of view fields of the windows 1207, 1208 is given by $\theta$=arctan ($l_5/l_4$–arctan ($l_5/(l_3+l_4)$). Given, for example, $l_3=2$ mm, $l_4=3$ mm, $l_5=0.1$ mm, g=0.1 mm, the view field angle $\theta$ becomes about 3.1°. Then the angle $\theta$ formed by the centers of view fields of windows 1207, 1208 through which the rays pass becomes 0.76°.

The permeating radioactive rays which have passed through 10 the windows 1207, 1208 respectively expand in radioactive ray areas shown by 1204, 1205 in the rear of lattice beard 1201. There exist areas where both of the radioactive rays overlap as the distance from the lattice board 1201 increases. However, the image pickup surface shown by 1206 of FIG. 12 is placed at a position where the radioactive ray areas 1204, 1205 are not overlapped, whereby two images of the permeated object different in their directivities of view field angles are separately formed on the image pickup surface 1206.

Embodiment 4

Figure 13:
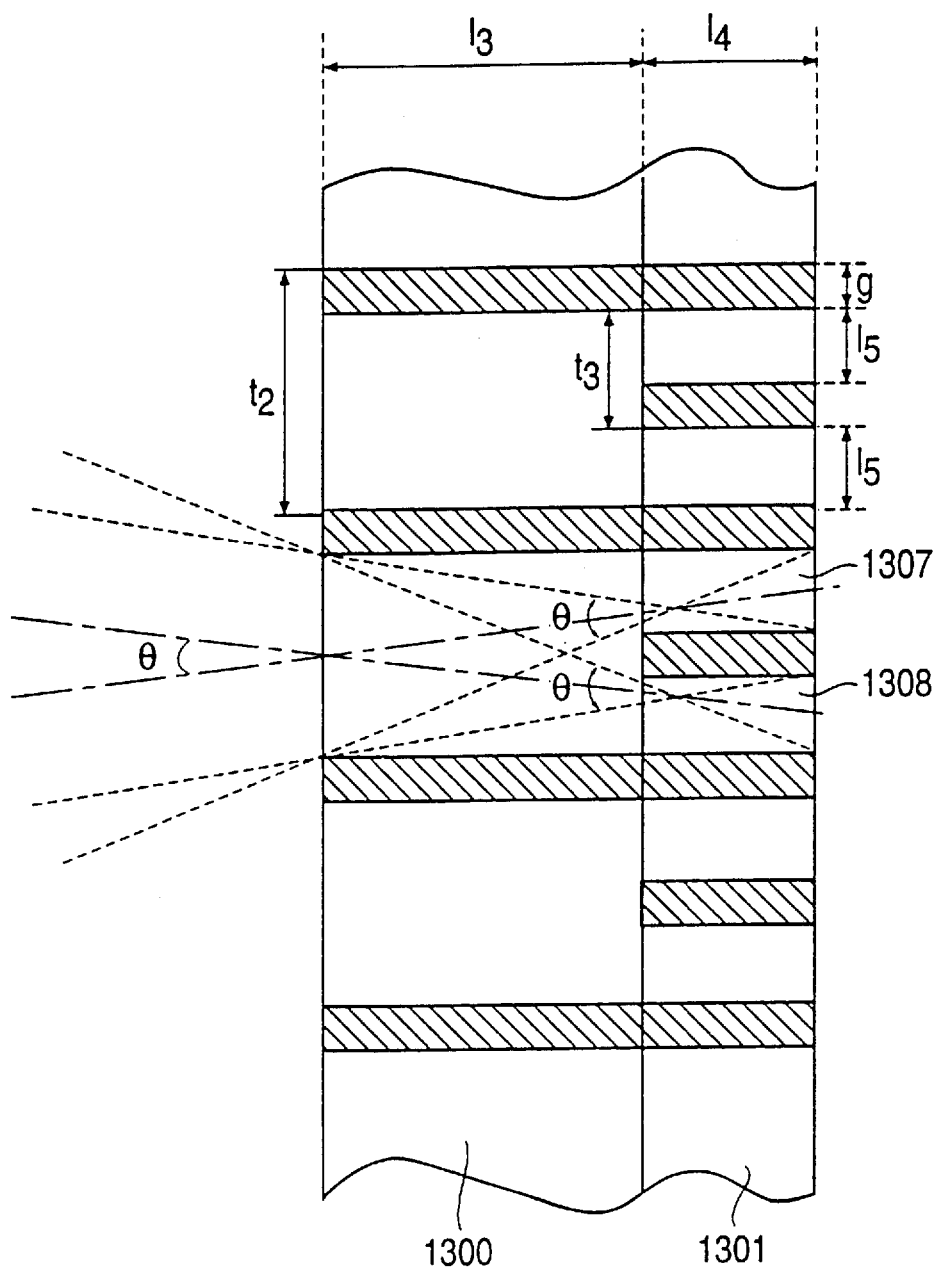
FIG. 13 is a block diagram of a lattice according to a fourth embodiment of the invention.

Referring to FIG. 13, a description will now be given of a lattice made by joining two sheets of lattice boards different in their pitches to let them have a plurality of directivities according to a fourth embodiment of the invention. This aspect refers to a case similar to the embodiment of FIG. 12 except that, in the embodiment of FIG. 13, ($l_3>l_4$) In other words, although the structure of this lattice is similar to that of the double lattice board of FIG. 12, the thickness $l_3$ (e.g., 3 mm) of a lattice board 1300 close to an object is set greater than the thickness $l_4$ (e.g., 2 mm) of a lattice board 1301 far from the object. Given the pitch $t_2$ (e.g., 0.4 mm) of the lattice board 1300, the pitch $t_3$ (e.g., 0.2 mm) of the lattice board 1301, and the breadth g (e.g., 0.1 mm) of the lead portions of the lattice, the view field angles $\theta$ of the windows 1307, 1308 of the lattice board 1301 through which the rays pass are given by $\theta$=arctan ($2l_5$+g)/($l_3+l_4$)+arctan ($l_5/(l_3+l_4)$). The angle $\theta$ formed by the centers of view fields of the windows 1307, 1308 is given by $\theta$=arctan ($2l_5$+g)/($l_3+l_4$)–arctan ($l_5/(l_3+l_4)$) . Given, for example, $l_3=3$ mm, $l_4=2$ mm, $l_5=0.1$ mm, g=0.1 mm, the view field angle $\theta$ becomes about 4.6° and the angle $\theta$ formed by the centers of view fields becomes 2.3°. In comparison with the case of $l_3<l_4$ of FIG. 12, the angle formed by the centers of the view fields becomes greater in contrast to the fact that the view field angle less expands. Consequently, the size relation between $l_3$ and $l_4$ shown in FIGS. 12 and 13 is determined by the positions of radioactive ray sources and the size of the view field angle at which the permeating radioactive rays are taken in.

Embodiment 5

Figure 14:
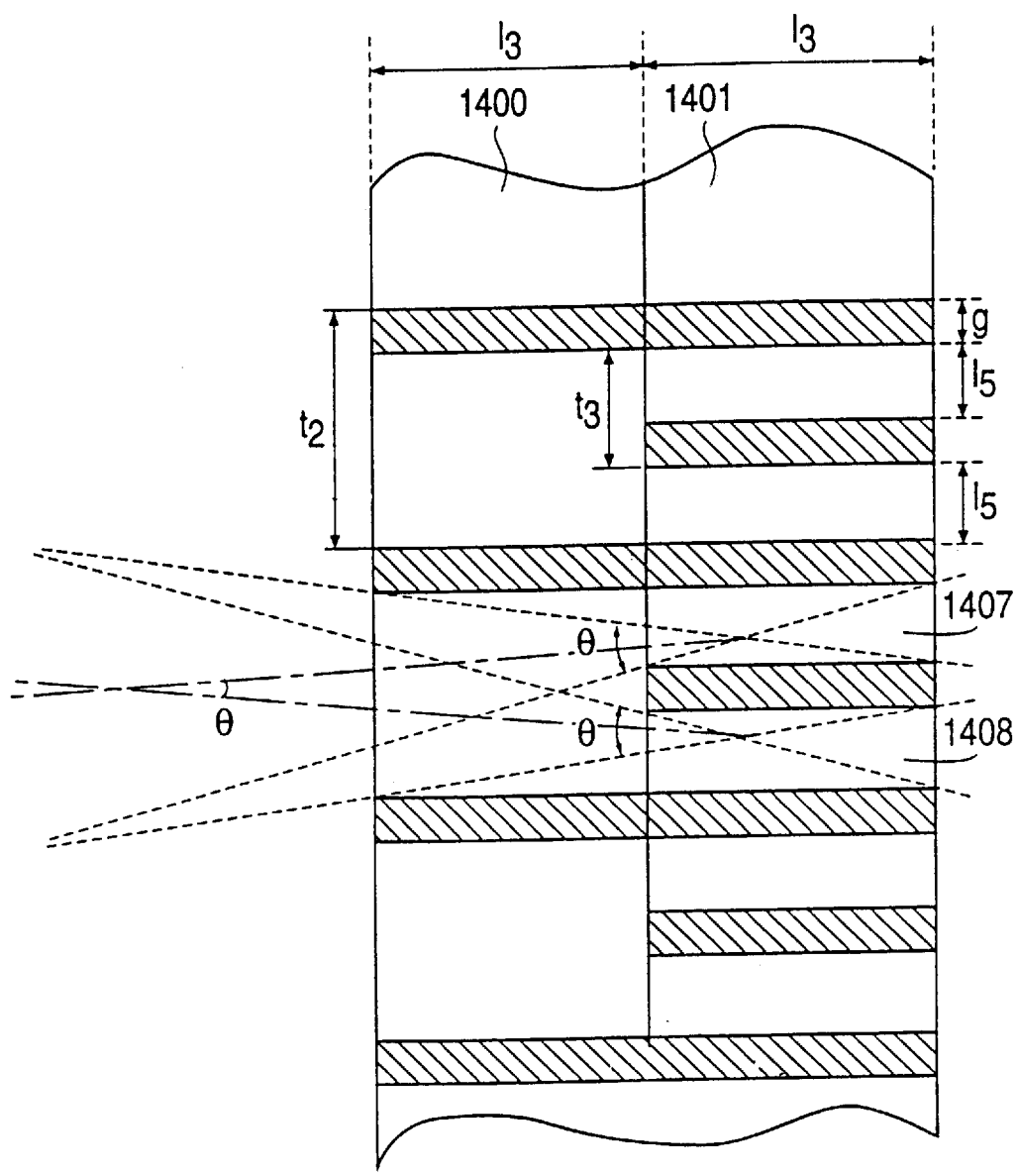
FIG. 14 is a block diagram of a lattice according to a fifth embodiment of the invention.

Referring to FIG. 14, a description will now be given of a lattice made by joining two sheets of lattice boards different in their pitches to let then have a plurality of directivities according to the fifth embodiment of the invention. This aspect refers to a case where, although the structure of this lattice is similar to that of the double lattice board of FIG. 12, the thicknesses $l_3$ (e.g., 3 mm) of two lattice boards 1400, 1401 are equal. Given the pitch $t_2$ (e.g., 0.4 mm) of the lattice board 1400, the pitch $t_3$ (e.g., 0.2 mm) of the lattice board 1401, and the breadth g (e.g., 0.1 mm) of the lattice, the view field angles $\theta$ of the windows 1407, 1408 of the double lattice board through which the rays pass are given by $\theta$=arctan ($l_5/l_3$)+arctan ($l_5/(2l_3)$). The angle $\theta$ formed by the centers of view fields of the windows 1407, 1408 is given by $\theta$=arctan ($l_5/l_3$)–arctan ($l_5/(2l_3)$). Given, for example, $l_3=3$ mm, $l_5=0.1$ mm, $g=0.1$ mm, the view field angle θ becomes 2.86° and the angle θ formed by the centers of view fields becomes 0.96°.

Embodiment 6

Figure 15:
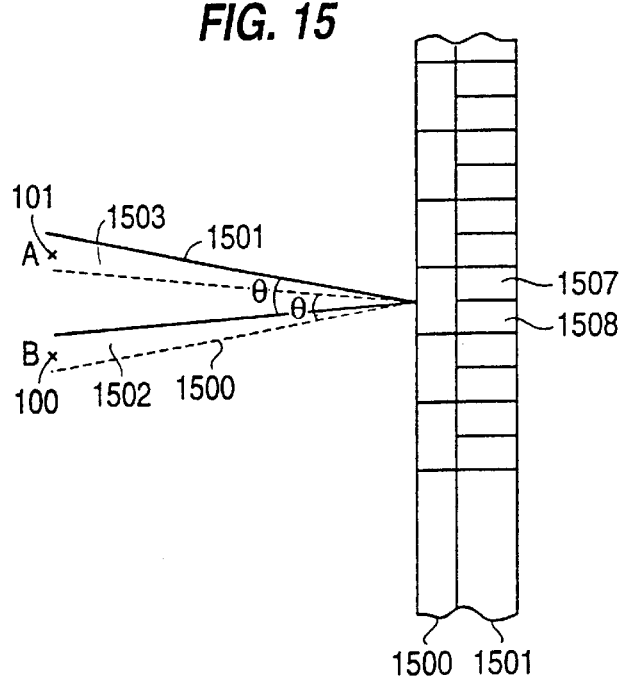
FIG. 15 is a block diagram of a lattice according to a sixth embodiment of the invention.

Referring to FIG. 15, a description will now be given of the condition of arranging radioactive ray sources for a lattice made by joining two sheets of lattice boards different in their pitches with reference to the third to fifth embodiment of the invention to let then have a plurality of directivities according to the sixth aspect thereof.

In FIG. 15, there is shown a window 1507 formed with lattice boards 1500, 1501 joined together and the direction 1500 of a view field, a window 1508 and the direction 1501 of a view field, and the relation between the positions of a plurality of radioactive ray sources A101, B100 and the view fields 1500, 1501. Although the two view fields 1500, 1501 share a spatial part for common use, the radioactive ray sources B100, A101 are arranged in spatial parts 1502, 1503 not for common use. Assuming the double lattice of FIG. 13 is set 2 mm apart from the two radioactive ray sources, the radioactive ray sources are placed 11.5 cm apart from each other. With this arrangement of the radioactive ray sources, the radioactive rays emitted from the radioactive ray source A101 are allowed to pass through only the window 1508 but not to pass through the window 1507. Likewise, the radioactive rays emitted from the radioactive ray source B100 are allowed to pass through only the window 1507 but not to pass through the window 1508. By arranging the plurality of radioactive ray sources in the respective areas which are formed by joining together lattices having different pitches and where the plurality of view fields are not overlapped, radioactive rays radiated from each radioactive ray source and permeated through an object make an image in the rear of each independent portion of the permeating window so as to form an image for pickup at the back of the lattice while separating images different in their angles deriving from the radioactive ray source.

Embodiment 7

Figure 16:
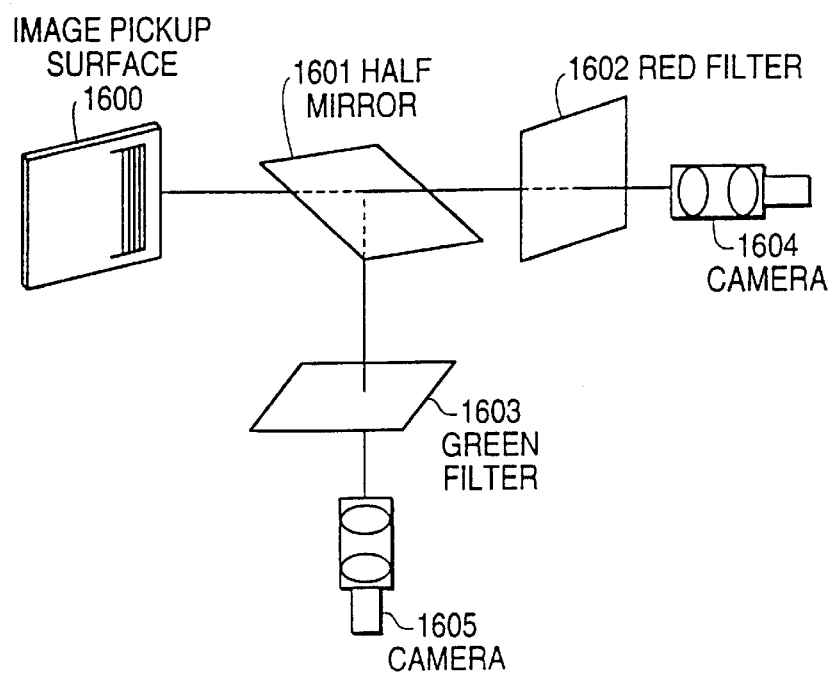
FIG. 16 is a block diagram of a lattice according to a seventh embodiment of the invention.

Referring to FIG. 16, a description will be given of at method of image processing according to a seventh embodiment of the invention. The method of image processing features that images are separated by utilizing differences among luminous colors of phosphors. Phosphors having different luminous colors, for example, red and green phosphors, are applied to the divided image pickup surface 1600 in stripes, and a half mirror is employed for separating an image having a mixed color into two images. The image thus separated from the other is passed through, for example, a red filter 1602 for filtering the same color as the luminous color (e.g., red) of a phosphor. As a result, red pixels on the image pickup surface are negated in a camera 1604 and only a green image is introduced, whereby the image is converted into electric signals therein.

On the other hand, the other image thus separated by the half mirror is passed through a green filter 1603 and what is formed on the image pickup surface in the camera 1605 becomes luminous in red only. This image is converted into electric signals. In this way, the plurality of striped luminous images of the phosphors are separated by means of the half mirror, and each of them is passed through the color filter having the same color as that of the phosphor, so that each of the images having the luminous colors corresponding to the colors of the respective phosphors is obtained. Therefore, the striped or dotted, divided luminous surfaces deriving from the X rays emitted from the plurality of light sources are painted with the phosphors different in their luminous colors, and the images from the respective radioactive ray sources are then separated.

According to this aspect of the invention, two colors of red and green have been employed for the luminous colors of the phosphors. However, more than two colors may obviously be used.

Embodiment 8

Figure 17A:
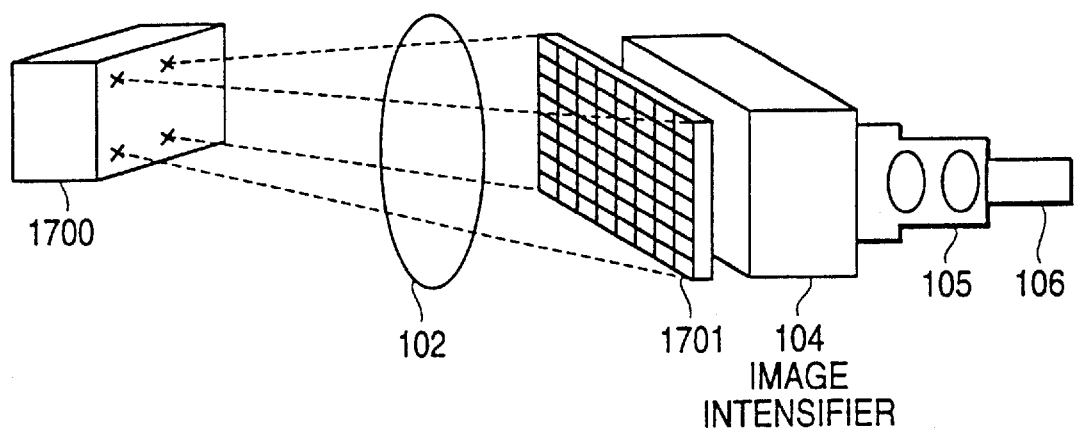
FIGS. 17(a) and 17(b) are diagrams illustrating a pickup and display method of a stereoscopic image according to an eighth embodiment of the invention.
Figure 17B:
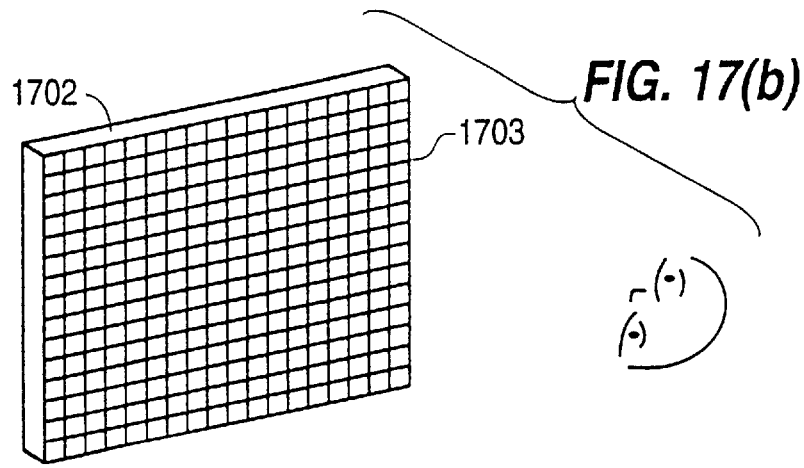

Referring to FIGS. 17(a), 17(b), a description will be given of a display method of stereoscopic images according to an eighth embodiment of the invention. The display method of stereoscopic images according to this aspect of the invention features that stereoscopic visual observation can be made in both the vertical and horizontal directions.

FIG. 17(a) shows the pickup method of a stereoscopic image that can be stereoscopically visualized in the vertical direction. A plurality of sources 1700 of radioactive rays such as X rays are arranged in the horizontal and also vertical directions. The distance between the X-ray sources is 63 mm in the horizontal direction and 31 mm, which is half the binocular distance, in the vertical direction. The radioactive rays from the planar radioactive ray sources are permeated through the object 102 and then passed through a meshed lattice 1701 so as to make an image in the pickup apparatus 104 in the form of I. I. in FIG. 17(a), for example. A dotted pattern is formed on the image pickup surface, which is picked up by the camera 106 via the optical lens system 105.

FIG. 17(b) refers to a case where a meshed lattice 1702 is installed near the surface of a display 1702 so as to permit observation of a stereoscopic image. In this case, the pitch of the lattice display 1702 is set at the value obtained by multiplying the pitch of the pickup lattice 1701 by a magnification at the time of display. Given, for example, the magnification=2, and the vertical resolution with a 40-inch display=1,000 lines, the vertical pitch of the lattice will be 1.2 mm. With this arrangement, the observer observes the stereoscopic image both horizontally and vertically with the naked eyes.

Although a meshed lattice has been fitted to the display in the example of FIG. 17(b), a striped lattice can be fitted to the display to provide a stereoscopic visual observation when the plurality of radioactive ray sources are arranged only in the horizontal direction to provide only a horizontal stereoscopic pickup display.

Embodiment 9

Figure 18:
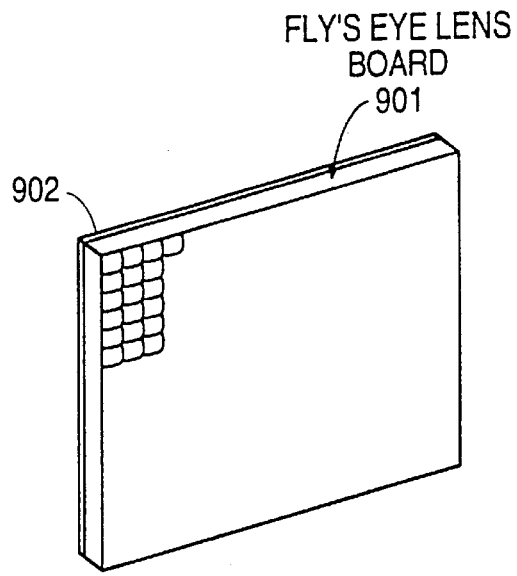
FIG. 18 a block diagram of a stereoscopic image display according to the seventh embodiment of the invention.

Referring to FIG. 18, a description will be given of a stereoscopic image display according to a ninth embodiment of the invention. The stereoscopic image display according to this aspect of the invention is fitted with a fly's eye lens board 901 on the surface of the display 902. The provision of the fly's eye lens board 901 makes possible both vertical and horizontal stereoscopic visual observation with sources of radioactive rays such as x rays and a meshed lattice. As in the case of the lenticular lens board, the lateral pitch of the fly's eye lens board is set the same as the pitch of a set of dotted patterns, whereas the vertical pitch thereof is set the same as the vertical pitch of the meshed lattice. Scanning lines on the image pickup surface are spaced at a value obtained by dividing the vertical spaces of the lattice by the number of radioactive ray sources. When three radioactive ray sources are vertically arranged, one fly's eye lens contains three scanning lines. By displaying the dotted pattern formed on the image pickup surface as it is on the display 902 and fitting the fly's eye lens board to the display, the observer can enjoy stereoscopic visual observation in not only the horizontal but also the vertical direction without using polarized glasses or the like.

Embodiment 10

Figure 19:
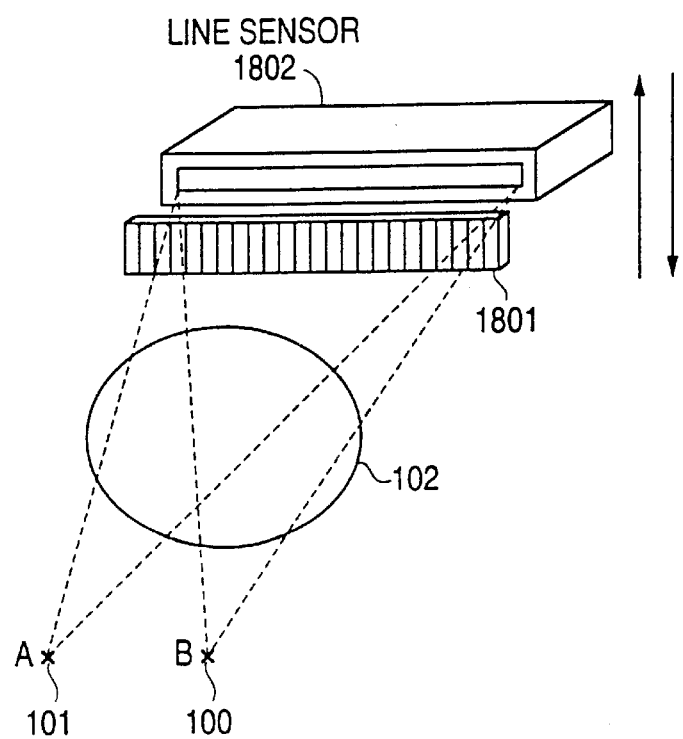
FIG. 19 is a diagram illustrating a pickup and display method of stereoscopic images from a permeated object.

Referring to FIG. 19, a description will be given of the pickup and display method of stereoscopic permeated images according to a tenth embodiment of the invention, wherein a line sensor 1802 is used as a pickup element. Radioactive rays are emitted from the two radioactive ray sources A101, B100 and the radioactive rays permeate through the object 102 and enter the line sensor 1802 after being spatially divided by a lattice 1802 with line-up stripes (e.g., the pitch of stripes=0.2 mm). A dotted pattern is formed on the image pickup surface on the line sensor. The line sensor 1802 and the lattice 1801 are vertically moved as viewed from FIG. 19 to obtain the image of the whole permeated object 102 as subsequent signals. In this case, only the object may be moved vertically. The image obtained subsequently is stored in a memory in the form of analog or digital signals.

The image of the permeated object is read from the memory at timing fit for the display, whereby the stereoscopic image is displayed. When the stereoscopic image is transmitted, the signals obtained from the line sensor are transmitted via a telephone circuit and the like. The signals thus transmitted are processed by a facsimile and the like on the receiver side, so that display is made of two sheets of plane images or otherwise an image capable of stereoscopic visual observation by means of the stereoscopic display.

As set forth above, the plurality of radioactive ray sources can simultaneously be operated. Therefore, not only the precise, deep stereoscopic image of a moving object but also a stereoscopic image of high picture quality with high brightness is made available through a simple method and apparatus.

It is to be understood that the above-described arrangements are simply illustrative of the application of the principles of this invention. Numerous other arrangements may be readily devised by those skilled in the art which embody the principles of the invention and fall within its spirit and scope.

We claim:

1. A pickup and display apparatus for stereoscopic images, said apparatus comprising:
   a plurality of radioactive ray sources capable of substantially simultaneously radiating a plurality of radioactive rays which are non-parallel with each other onto an object to permeate the object to generate a plurality of superimposed images of the object;
   means for spatially separating the plurality of superimposed images to prevent the images from overlapping and dividing each image into a plurality of discrete partial images to be formed on a pickup surface of an image pickup device;
   means for reconstructing a stereoscopic image of the object by processing the partial images; and
   means for stereoscopically displaying the stereoscopic image,
   wherein the means for separating and dividing the superimposed images is capable of being located between the object and the pickup surface of image pickup device,
   wherein the means for reconstructing the stereoscopic image is electrically connected with the pickup surface of the image pickup device, and
   wherein the means for stereoscopically displaying the stereoscopic image is capable of being located at a position where it is optically coupled to the means for reconstructing the stereoscopic image, said apparatus includes two radioactive ray sources, and means for setting up the view point of an observer at a distance D derived from the distance X between the two radioactive ray sources and a radioactive ray receiving part of the object such that:

$$X=\beta(D/\alpha-d)/(1-\beta)$$

where $\beta=\alpha L/P$, $\beta \neq 1$, given the distance between the two radioactive ray sources=2L, the distance from the two radioactive ray sources for radiating the plurality of radioactive rays up to the pickup surface of the image pickup device=d, the distance from the observer up to a display screen=D, a length of the image on the screen of the display to a length of the image on the pickup surface of the image pickup device=$\alpha$, and a distance between binocular eyes of the observer=2P.

2. A pickup and display apparatus for stereoscopic images as claimed in claim 1, said apparatus including means for sampling each one of the partial images on the surface of the image pickup device and converting the partial images into digital signals.

3. A pickup and display apparatus for stereoscopic images as claimed in claim 1, wherein the means for separating and dividing the superimposed images comprises a lattice arranged with a striped material capable of stopping the radioactive rays.

4. A pickup and display apparatus for stereoscopic images as claimed in claim 3, wherein the breadth g of the lattice material has the following value:

$$g>(2L+l_2)\{l_2(d'+l_1)-2Ll_1\}/\{(2L-l_2)(d'+l_1)\}$$

given the length of the lattice material for stopping radioactive rays in the thickness direction=$l_1$, the breadth of the lattice material=g, the breadth of a portion through which the radioactive rays pass=$l_2$; the distance between the two radioactive ray sources=2L, and the distance from the two radioactive ray sources up to an incident surface of the lattice=d'.

5. A pickup and display apparatus for stereoscopic images as claimed in claim 4, wherein the distance x between the lattice and the pickup surface is in the range of $x_1 \leq x \leq x_2$ where
   $x_1=(l_2(d'+l_1)-2Ll_1)/(2L-l_2)$,
   $x_2=g(d'+l_1)/(2L+l_2)$.

6. A pickup and display apparatus for stereoscopic images as claimed in claim 3, wherein the lattice is formed by overlapping a plurality of striped lattices with different pitches.

7. A pickup and display apparatus for stereoscopic images as claimed in claim 6, wherein the pitch of the one of the lattices close to the object is wider than that of another of the lattices farther from the object.

8. A pickup and display apparatus for stereoscopic images as claimed in claim 6, wherein, given the pitch of the lattice close to the object=$t_2$ and that of the lattice far from the object=$t_3$, the relation of $mt_2=nt_3$ is justified when positive numbers m, n (m<n) are used.

9. A pickup and display apparatus for stereoscopic images as claimed in claim 3, wherein the pickup surface of the image pickup device is formed with a line sensor arranged to receive radioactive rays spatially divided by the striped lattice.

10. A pickup and display apparatus according to claim 3, wherein the material capable of stopping the radioactive rays is comprised of lead.

11. pickup and display apparatus for stereoscopic images as claimed in claim 1, wherein the radioactive rays are particle rays having charge which are electrons or ionized particles, and wherein the lattice is formed with stripe or mesh shaped electrodes.

12. A pickup and display apparatus for stereoscopic images as claimed in claim 1, wherein the pickup surface of the image pickup device is painted with a plurality of phosphors having different luminous colors.

13. A pickup and display apparatus for stereoscopic images as claimed in claim 12, wherein color filters are provided having the same color as that of the corresponding phosphor.

14. A pickup and display apparatus for stereoscopic images as claimed in claim 1, said apparatus including at least a lenticular lens, a fly's eye lens or a meshed lattice.

15. A pickup and display apparatus for stereoscopic images, said apparatus comprising:
 a plurality of radioactive ray sources capable of substantially simultaneously radiating a plurality of radioactive rays which are non-parallel with each other onto an object to permeate the object to generate a plurality of superimposed images of the object;
 means for spatially separating the plurality of superimposed images to prevent the images from overlapping and dividing each image into a plurality of discrete partial images to be formed on a pickup surface of an image pickup device;
 means for reconstructing a stereoscopic image of the object by processing the partial images; and
 means for stereoscopically displaying the stereoscopic image,
 wherein the means for separating and dividing the superimposed images is capable of being located between the object and the pickup surface of image pickup device,
 wherein the means for reconstructing the stereoscopic image is electrically connected with the pickup surface of the image pickup device, and
 wherein said apparatus includes two radioactive ray sources, and means for setting up the distance between the two radioactive ray sources, and a dilatation ratio of a length of the image on a screen of the display to a length of the image on the pickup surface of the image pickup device in such a way as to make them conform to substantially $\alpha L = P$, given the distance between the two radioactive ray sources=$2L$, the distance between human binocular eyes=$2P$, and the dilatation ratio=$\alpha$.

16. A pickup and display apparatus for stereoscopic images as claimed in claim 15, said apparatus including means for setting up the position of an observer in such a manner as to satisfy substantially $D=\alpha d$ under the condition of $P=\alpha L$, given the distance from the plurality of radioactive ray sources for radiating the plurality of radioactive rays up to the pickup surface of the image pickup device=$d$, and the distance from the observer up to a display screen=$D$.

17. A pickup and display apparatus for stereoscopic images as claimed in claim 15, said apparatus including means for sampling each one of the partial images on the pickup surface of the image pickup device and converting the partial images into digital signals.

18. A pickup and display apparatus for stereoscopic images as claimed in claim 15, wherein the means for separating and dividing the superimposed images comprises a lattice arranged with a striped material capable of stopping the radioactive rays.

19. A pickup and display apparatus for stereoscopic images as claimed in claim 18, wherein the breadth g of the lattice material has the following value:

$$g > (2L+l_2)\{l_2(d'+l_1)-2Ll_1\}/\{(2L-l_2)(d'+l_1)\}$$

given the length of the lattice material for stopping radioactive rays in the thickness direction=$l_1$, the breadth of the lattice material=$g$, the breadth of a portion through which the radioactive rays pass=$l_2$; the distance between the two radioactive ray sources=$2L$, and the distance from the two radioactive ray sources up to an incident surface of the lattice=$d'$.

20. a pickup and display apparatus for stereoscopic images as claimed in claim 19, wherein the distance x between the lattice and the pickup surface is in the range of $x_1 \leq x \leq x_2$
where
 $x_1=(l_2(d'+l_1)-2Ll_1)/(2L-l_2)$,
 $x_2=g(d'+l_1)/(2L+l_2)$.

21. A pickup and display apparatus for stereoscopic images as claimed in claim 18, wherein the lattice is formed by overlapping a plurality of striped lattices with different pitches.

22. A pickup and display apparatus for stereoscopic images as claimed in claim 21, wherein the pitch of the one of the lattices close to the object is wider than that of another of the lattices farther from the object.

23. A pickup and display apparatus for stereoscopic images as claimed in claim 21, wherein, given the pitch of the lattice close to the object=$t_2$ and that of the lattice far from the object=$t_3$, the relation of $mt_2=nt_3$ is justified when positive numbers m, n (m<n) are used.

24. A pickup and display apparatus for stereoscopic images as claimed in claim 18, wherein the pickup surface of the image pickup device is formed with a line sensor arranged to receive radioactive rays spatially divided by the striped lattice.

25. A pickup and display apparatus according to claim 18, wherein the material capable of stopping the radioactive rays is comprised of lead.

26. A pickup and display apparatus for stereoscopic images as claimed in claim 15, wherein the radioactive rays are particle rays having charge which are electrons or ionized particles, and wherein the lattice is formed with stripe or mesh shaped electrodes.

27. A pickup and display apparatus for stereoscopic images as claimed in claim 15, wherein the pickup surface of the image pickup device is painted with a plurality of phosphors having different luminous colors.

28. A pickup and display apparatus for stereoscopic images as claimed in claim 27, wherein color filters are provided having the same color as that of the corresponding phosphor.

29. A pickup and display apparatus for stereoscopic images as claimed in claim 15, said apparatus including at least a lenticular lens, a fly's eye lens or a meshed lattice.

* * * * *